(12) United States Patent
Linclau

(10) Patent No.: US 8,183,394 B2
(45) Date of Patent: May 22, 2012

(54) PROTEASE INHIBITOR PRECURSOR SYNTHESIS

(75) Inventor: Bruno Linclau, Southampton (GB)

(73) Assignee: Tibotec Pharmaceuticals Ltd., Little Island (IE)

( * ) Notice: Subject to any disclaimer, the term of this patent is extended or adjusted under 35 U.S.C. 154(b) by 0 days.

(21) Appl. No.: 13/280,822

(22) Filed: Oct. 25, 2011

(65) Prior Publication Data

US 2012/0041215 A1 Feb. 16, 2012

Related U.S. Application Data

(62) Division of application No. 11/816,607, filed as application No. PCT/EP2006/060246 on Feb. 24, 2006, now Pat. No. 8,067,463.

(60) Provisional application No. 60/683,699, filed on May 23, 2005.

(30) Foreign Application Priority Data

Feb. 25, 2005 (EP) .................................. 05101462

(51) Int. Cl.
C07F 7/02 (2006.01)
(52) U.S. Cl. ...................................................... 549/214
(58) Field of Classification Search .................. 549/214
See application file for complete search history.

(56) References Cited

FOREIGN PATENT DOCUMENTS

| | | |
|---|---|---|
| EP | 1 265 073 A2 | 12/2002 |
| WO | WO 99/67254 A2 | 12/1999 |
| WO | WO 99/67417 A2 | 12/1999 |
| WO | WO 01/24240 A1 | 4/2001 |
| WO | WO 01/25240 A1 | 4/2001 |
| WO | WO 02/081478 A2 | 10/2002 |
| WO | WO 02/083657 A2 | 10/2002 |
| WO | WO 02/092595 A1 | 11/2002 |
| WO | WO 03/049746 A2 | 6/2003 |
| WO | WO 03/053435 A1 | 7/2003 |
| WO | WO 03/057173 A2 | 7/2003 |
| WO | WO 03/064406 A1 | 8/2003 |
| WO | WO 03/070976 A2 | 8/2003 |
| WO | WO 03/076413 A1 | 9/2003 |
| WO | WO 03/078438 A1 | 9/2003 |
| WO | WO 03/090690 A2 | 11/2003 |
| WO | WO 03/090691 A2 | 11/2003 |
| WO | WO 03/097616 A1 | 11/2003 |
| WO | WO 03/106461 A2 | 12/2003 |
| WO | WO 2004/003817 A1 | 1/2004 |

OTHER PUBLICATIONS

Ohtaka, H. et al., "Overcoming drug resistance in HIV-1 chemotherapy: The binding thermodynamics of Amprenavir and TMC-126 to wild-type and drug resistant mutants of the HIV-1 protease", Protein Science (2002), vol. 11, pp. 1908-1916.

Gatanaga, H. et al., "Amino Acid Substitutions in Gag Protein at Non-cleavage Sites are Indispensable for the Development of a High Multitude of HIV-1 Resistance against Protease Inhibitors", Journal of Biological Chemistry, (2002), vol. 277, No. 8, pp. 5952-5961.

Ghosh, A. et al, "Antiviral activity of UIC-PI, a novel inhibitor of the human immunodeficiency virus type 1 protease", Antiviral Research, (2002), vol. 54, No. 1, pp. 29-36.

Yoshimura, K. et al., "A Potent Human Immunodeficjency Virus Type 1 Protease Inhibitor, UIC-94003 (TMC-126), and Selection of a Novel (A28S) Mutation in the Protease Active Site", Journal of Virology, (2002), vol. 76, No. 3, pp. 1349-1358.

Ghosh, A., et al., "Structure-based design of non-peptide HIV protease ihhibitors", IL Farmaco, (2001), vol. 56, Nos. 1-2, pp. 29-32.

Ghosh, A., et al., "Potent HIV Protease Inhibitors Incorporating High-Affinity P$_2$-Ligands and (R)-(Hydroyxethylamino)Sulfonamide Isostere", Bioorganic & Medicinal Chemistry Letters, (1998), vol. 8, No. 6, pp. 687-690.

Ghosh, A., et al., "Nonpeptidal P$_2$ Ligands for HIV Protease Inhibitors: Structure-Based Design, Synthesis, and Biological Evaluation", Journal of Medicinal Chemistry, (1996), vol. 39, pp. 3278-3290.

Koh, Y., et al., "Novel bis-Tetrahydrofuranylurethane-Containing Nonpeptidic Protease Inhibitor (PI) UIC-94017 (TMC114) with Potent Activity against Multi-PI-Resistant Human Immunodeficiency Virus In Vitro", Antimicrobial Agents and Chemotherapy, (2003), vol. 47, No. 10, pp. 3123-3129.

Trost, B.M. et al., "Comprehensive Organic Synthesis", Pergamon Press, (1991), vol. 7, pp. 291-303.

Tidwell, T.T., "Oxidation of Alcohols by Activated Dimethyl Sulfoxide and Related Reactions: An Update", Synthesis, (1990), vol. 1990, No. 10, pp. 857-870.

Tidwell, T.T., "Oxidation of Alcohols to Carbonyl Compounds Via Alkoxysulfonium Ylides: The Moffatt, Swern, and Related Oxidations", Organic Reactions, (1990), vol. 39, pp. 297-557.

Parikh, J.R., et al., "Sulfur Trioxide in the Oxidation of Alcohols by Dimethyl Sulfoxide", Journal of the American Chemical Society, (1967), vol. 89, No. 21, pp. 5505-5507.

Mancuso, A.J., et al., "Activated Dimethyl Sulfoxide: Useful Reagents for Synthesis", Synthesis, (1981), vol. 1981, No. 3, pp. 165-185.

Pfitzner, K.E., et al., "The Synthesis of Nucleoside-5' Aldehydes", Journal of the American Chemical Society, (1963), vol. 85, p. 3027.

Maleczka, R.E., et al., "Total Synthesis of Proposed Amphidinolide A via a Highly Selective Ring-Closing Metathesis", Organic Letters, (2002), vol. 4, No. 17, pp. 2841-2844.

Linclau, B., et al., "Efficient Desymmetrization of "Pseudo"-C$_2$-Symmetric Substrates: Illustration in the Synthesis of a Disubstituted Butenolide from Arabitol", Journal of Organic Chemistry, (2003), vol. 68, No. 5, pp. 1821-1826.

International Search report for Application No. PCT/EP2006/060246 mailed Jul. 26, 2006.

*Primary Examiner* — Taofiq A Solola

(57) ABSTRACT

The present invention provides a compound having the structure (I) and processes for the production thereof and the intermediates used in such process.

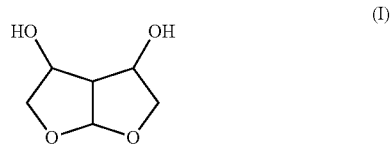

(I)

10 Claims, No Drawings

US 8,183,394 B2

PROTEASE INHIBITOR PRECURSOR SYNTHESIS

CROSS REFERENCE TO RELATED APPLICATIONS

This application is a divisional of U.S. patent application Ser. No. 11/816,607, filed May 20, 2008, now U.S. Pat. No. 8,067,463 which is a national stage of PCT Application No. PCT/EP2006/060246, filed Feb. 24, 2006, which claims priority from European Patent Application No. 05101462.9, filed Feb. 25, 2005, which claims priority from U.S. Provisional Application Ser. No. 60/683,699, filed May 23, 2005, all of which are hereby incorporated by reference in their entirety.

FIELD OF INVENTION

The present invention relates to compounds and processes for their preparation, which are useful in the production of protease inhibitors, in particular broad spectrum HIV protease inhibitors.

BACKGROUND OF INVENTION

HIV infection remains a major medical problem. Currently available HIV drugs include nucleoside reverse transcriptase (RT) inhibitors, non-nucleoside reverse transcriptase inhibitors as well as peptidomimetic protease inhibitors. Each of these drugs can only transiently restrain viral replication if used alone. Insufficient drug potency, non-compliance, restricted tissue penetration and drug-specific limitations within certain cell types may account for the incomplete suppression of sensitive viruses.

Furthermore, HIV is an extremely heterogeneous virus. The clinical significance of this heterogeneity is evidenced by the ability of the virus to evade immunological pressure, survive drug selective pressure, and adapt to a variety of cell types and growth conditions. Therefore, diversity is a major obstacle to pharmacologic or immunologic control of human immunodeficiency virus infection.

One of the critical pathways in a retroviral life cycle is the processing of polyprotein precursors by aspartic protease. For instance with the HIV virus the gag-pol protein is processed by HIV protease. The correct processing of the precursor polyproteins by the aspartic protease is required for the assembly of infectious virions, thus making the aspartic protease an attractive target for antiviral therapy. In particular for HIV treatment, the HIV protease is an attractive target.

HIV protease inhibitors (PIs) are commonly administered to AIDS patients in combination with other anti-HIV compounds such as, for instance nucleoside reverse transcriptase inhibitors (NRTIs), non-nucleoside reverse transcriptase inhibitors (NNRTIs), nucleotide reverse transcriptase inhibitors (NtRTIs) or other protease inhibitors. Despite the fact that these antiretrovirals are very useful, they have a common limitation, namely, the targeted enzymes in the HIV virus are able to mutate in such a way that the known drugs become less effective, or even ineffective against these mutant HIV viruses. Or, in other words, the HIV virus creates an ever increasing resistance against the available drugs.

In search of compounds that are able to meet the medical need in HIV treatment, sulfonamide derivatives of general formula (A) have been prepared and are found to have a broad virological spectrum with little variance in fold resistance, i.e. difference in viral inhibitory activity on HIV wild-type and HIV mutant strains (WO 2004003817, WO 2003106461, WO 2003097616, WO 2003090691, WO 2003090690, WO 2003078438, WO 2003076413, WO 2003070976, WO 2003064406, WO 2003057173, WO 2003053435, WO 2003049746, EP 1265073, WO 2002092595, WO 2002083657, WO 2002081478, WO 2001025240, WO 9967417, WO 9967254, Ohtaka et al. Protein Science (2002), 11(8), 1908-1916, Gatanaga et al. Journal of Biological Chemistry (2002), 277(8), 952-5961, Ghosh et al. Antiviral Research (2002), 54(1), 29-36, Yoshimura et al. Journal of Virology (2002), 76(3), 1349-1358, Ghosh et al. Farmaco (2001), 56(1-2), 29-32, Ghosh et al. Bioorganic & Medicinal Chemistry Letters (1998) 8(6) 687-690)

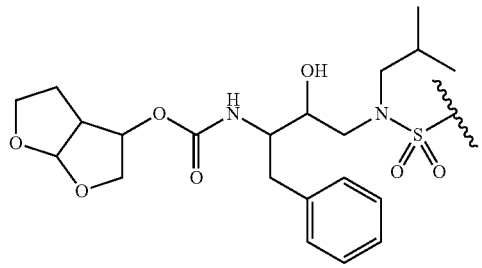

(A)

Despite the obtained results in the art, there is a continuous need for improved HIV protease inhibitors. Such improved HIV protease inhibitors can only be made if the knowledge on the medicinal chemistry allows the preparation of chemical variants. Compounds of general formula (A) are prepared in the art via a coupling reaction using hexahydro-furo[2,3-b]furan-3-ol as an intermediate. Further exploration of the hexahydro-furo[2,3-b]furan pharmacophore as a scaffold for new and improved HIV protease inhibitors has been prevented thus far because of a lack of knowledge on how to prepare substituted variants of hexahydro-furo[2,3-b]furan-3-ol.

SUMMARY OF THE INVENTION

According to a first aspect of the present invention, there is provided a compound having the structure (I) including its stereoisomers and salts.

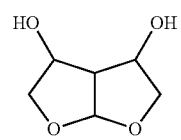

(I)

According to a second aspect of the present invention, there is provided a compound having the formula (II) including its stereoisomers and salts

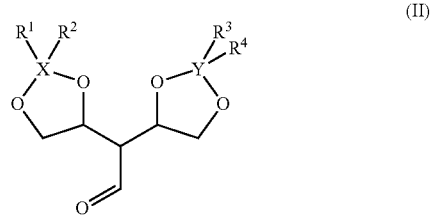

(II)

wherein

X and Y are independently selected from Si and C; and, $R^1$, $R^2$, $R^3$ and $R^4$ are independently selected from the group consisting of —H and monovalent hydrocarbon radicals.

According to a third aspect of the present invention, there is provided a compound having the formula (III) including its stereoisomers and salts

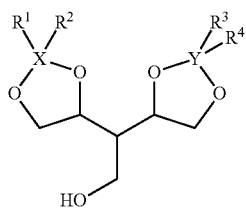

(III)

wherein

X and Y are independently selected from Si and C; and, $R^1$, $R^2$, $R^3$ and $R^4$ are independently selected from the group consisting of —H and monovalent hydrocarbon radicals.

According to a fourth aspect of the present invention, there is provided a compound having the formula (IV) including its stereoisomers and salts

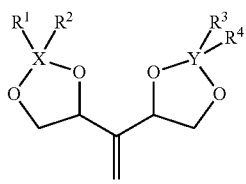

(IV)

X and Y are independently selected from Si and C; and, $R^1$, $R^2$, $R^3$ and $R^4$ are independently selected from the group consisting of —H and monovalent hydrocarbon radicals.

According to a fifth aspect of the present invention, there is provided a process for the production of a compound having the structure (I) comprising submitting a compound having the formula (II) to alcohol deprotection conditions and the thus formed deprotected intermediate undergoes an intramolecular cyclisation.

According to a sixth aspect of the present invention, there is provided a process for the production of a compound having the formula (II), comprising oxidising a compound having the formula (III).

According to a seventh aspect of the present invention, there is provided a process for the production of a compound having the formula (III), comprising hydroborating a compound having the formula (IV) and subsequently oxidising the thus formed hydroborated intermediate.

According to an eighth aspect of the present invention, there is provided a process for the production of a compound having the formula (IV), comprising reacting a compound having the formula (V) or a stereoisomer or salt thereof

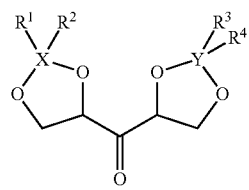

(V)

wherein

X and Y are independently selected from Si and C; and, $R^1$, $R^2$, $R^3$ and $R^4$ are independently selected from the group consisting of —H and monovalent hydrocarbon radicals; with a Wittig type reagent.

In the above mentioned compounds of formula (II), (III), (IV) and (V), $R^1$ and $R^2$ can also be taken together and form a bivalent hydrocarbon radical represented by —$R^1$-$R^2$—. Likewise, $R^3$ and $R^4$ can also be taken together and form a bivalent hydrocarbon radical represented by —$R^3$-$R^4$—.

DETAILED DESCRIPTION OF THE INVENTION

The term "stereoisomer" refers to a member of a family of compounds which have the same molecular formula (same number and kind of atoms), and have the same connectivity, but differ in the arrangement of the atoms in space. Stereoisomers include enantiomers and diastereomers.

As used herein, the term "monovalent hydrocarbon radicals" refers to any monovalent cyclic, heterocyclic, straight chain, branched chain, saturated or unsaturated radical, which contains a carbon backbone comprising one or more hydrogen atoms, optionally with one or more heteroatoms in the carbon backbone. The term "monovalent hydrocarbon radical" is intended to encompass the terms "alkyl", "alkenyl", "alkynyl", "cycloalkyl", "cycloalkenyl", "cycloalkynyl", "alkoxyalkyl", "alkoxyaryl", "(cycloalkyl)alkyl", "(cycloalkenyl)alkyl", "(cycloalkynyl)alkyl", "heterocyclylalkyl", "alkylheterocyclyl", "heterocyclyl", "alkylaryl", "arylalkyl" and "aryl" as defined below.

As used herein, the term "alkyl" as a group or part of a group refers to a straight or branched saturated monovalent hydrocarbon radical, having the number of carbon atoms as indicated, optionally substituted with a halogen. For example, $C_{1-3}$alkyl as a group or part of a group defines straight or branched chain saturated hydrocarbon radicals having from 1 to 3 carbon atoms such as methyl, difluoromethyl, ethyl, 1-chloroethyl, propyl, 1-methylethyl and the like; $C_{1-4}$alkyl as a group or part of a group defines straight or branched chain saturated hydrocarbon radicals having from 1 to 4 carbon atoms such as the group defined for $C_{1-3}$alkyl and butyl, 2-bromobutyl and the like; $C_{2-4}$alkyl as a group or part of a group defines straight or branched chain saturated hydrocarbon radicals having from 2 to 4 carbon atoms such as ethyl, propyl, 2-chloropropyl, 1-methylethyl, butyl and the like; $C_{1-6}$alkyl as a group or part of a group defines straight or branched chain saturated hydrocarbon radicals having from 1 to 6 carbon atoms such as the groups defined for $C_{1-4}$alkyl and pentyl, hexyl, 2-methylbutyl, 2-chloro-1-methylbutyl and the like; $C_{1-9}$alkyl as a group or part of a group defines straight or branched chain saturated hydrocarbon radicals having from 1 to 9 carbon atoms such as the groups defined for $C_{1-6}$alkyl and heptyl, 3-fluoro-heptyl, octyl, nonyl, 2-methylhexyl, 2-methylheptyl, decyl and the like; $C_{1-10}$alkyl as a group or part of a group defines straight or branched chain saturated hydrocarbon radicals having from 1 to 10 carbon atoms such as the groups defined for $C_{1-9}$alkyl and decyl, 2-methylnonyl, 4-bromo-decyl and the like; $C_{1-20}$alkyl as a group or part of a group defines straight or branched chain hydrocarbon radicals having from 1 to 20 carbon atoms such as the ones for $C_{1-10}$alkyl and undecyl, dodecyl, 2-ethyl-3-chlorododecyl and the like.

As used herein, the term "alkenyl" as a group or part of a group refers to a straight or branched unsaturated or partially unsaturated monovalent hydrocarbon radical, having the number of carbon atoms as indicated and the distinguishing feature of a carbon-carbon double bond. For example, the term $C_{2-3}$alkenyl as a group or part of a group defines hydrocarbon radicals having 2 or 3 carbon atoms containing at least one double bond such as, for example, ethenyl, propenyl, and the like; the term "$C_{2-5}$alkenyl" as a group or part of a group defines hydrocarbon radicals having from 2 to 5 carbon atoms containing at least one double bond such as the groups defined for $C_{2-3}$alkenyl, butenyl, pentenyl and the like; the term "$C_{2-6}$alkenyl" as a group or part of a group defines straight and branched chained hydrocarbon radicals having from 2 to 6 carbon atoms containing at least one double bond such as the groups defined for $C_{2-5}$alkenyl, hexenyl and the like; $C_{2-20}$alkenyl is a straight or branched hydrocarbon radical having from 2 to 20 carbon atoms and having at least one double carbon-carbon bond.

As used herein, the term "alkynyl" as a group or part of a group refers to a straight or branched unsaturated or partially unsaturated monovalent hydrocarbon radical, having the number of carbon atoms as indicated and the distinguishing feature of a carbon-carbon triple bond. For example, the term $C_{2-3}$alkynyl as a group or part of a group defines hydrocarbon radicals having 2 or 3 carbon atoms containing at least one triple bond such as, for example, ethynyl, propynyl and the like; the term $C_{2-5}$alkynyl as a group or part of a group defines straight and branched chained hydrocarbon radicals having from 2 to 5 carbon atoms containing at least one triple bond such as the groups defined for $C_{2-3}$alkynyl, butynyl, pentynyl and the like; the term $C_{2-6}$alkynyl as a group or part of a group defines straight and branched chained hydrocarbon radicals having from 2 to 6 carbon atoms containing at least one triple bond such as the groups defined for $C_{2-5}$alkynyl, hexynyl and the like; $C_{2-20}$alkynyl is a straight or branched hydrocarbon radical having from 2 to 20 carbon atoms and having at least one triple carbon-carbon bond.

As used herein, the term "cycloalkyl" as a group or part of a group refers to a cyclic saturated monovalent hydrocarbon radical, having the number of carbon atoms as indicated. For example, the term $C_{3-6}$cycloalkyl as a group or part of a group is generic to cyclopropyl, cyclobutyl, cyclopentyl, cyclohexyl; the term $C_{3-7}$cycloalkyl as a group or part of a group is generic to cyclopropyl, cyclobutyl, cyclopentyl, cyclohexyl, cycloheptyl; $C_{3-30}$cycloalkyl is a cyclic saturated monovalent hydrocarbon radical having from 3 to 30 carbon atoms.

As used herein, the terms "cycloalkenyl" and "cycloalkynyl" as a group or part of a group refer to cyclic unsaturated or partially unsaturated monovalent hydrocarbon radicals. A cycloalkenyl is characterized by at least one carbon-carbon double bond and a cycloalkynyl is characterized by at least one carbon-carbon triple bond. For example, $C_{3-30}$cycloalkenyl is a cyclic unsaturated monovalent hydrocarbon radical having from 3 to 30 carbon atoms and having at least one carbon-carbon double bond. Also by way of example, $C_{8-30}$cycloalkynyl is a cyclic unsaturated or partially unsaturated monovalent hydrocarbon radical having from 8 to 30 carbon atoms and having at least one carbon-carbon triple bond.

As used herein, the term "aryl" as a group or part of a group refers to a cyclic aromatic monovalent hydrocarbon radical such as phenyl and naphthyl, optionally substituted with one or more substituents such as for instance an alkyl group, an alkyloxy group or a alkanediyl group. A typical example of an aryl substituted with an alkanediyl group, the latter being defined as a bivalent alkyl group, is for instance indane. Where the aryl group comprises more than one ring, the rings may be fused, bicyclic or substituted with phenyl, for instance, biphenyl is also meant to be included in the definition of aryl. From the above definition, it should be clear that the entire aryl group does not necessarily have to be aromatic, but that it contains at least one aromatic moiety, such as, for example, indane. Also by way of example, $C_{6-30}$aryl is an cyclic aromatic hydrocarbon radical having from 6 to 30 carbon atoms.

As used herein, the term "heterocyclyl" as a group or part of a group refers to a cyclic saturated, partially saturated or aromatic monovalent hydrocarbon radical having at least one heteroatom in the backbone of such cyclic hydrocarbon, optionally substituted with one or more substituents such as for instance an alkyl group or an alkyloxygroup. Examples of heterocycles include but are not limited to dihydroisoxazolyl, furanyl, pyridyl, phthalimido, thienyl, pyrrolyl, imidazolyl, pyrazolyl, thiazolyl, isothiazolyl, oxazolyl, pyrrolidinyl, pyrrolinyl, imidazolidinyl, imidazolinyl, pyrazolidinyl, tetrahydrofuranyl, pyranyl, pyronyl, pyrazinyl, pyridazinyl, piperidinyl, piperazinyl, morpholinyl, thionaphthyl, benzofuranyl, isobenzofuryl, indolyl, oxyindolyl, isoindolyl, indazolyl, indolinyl, 7-azaindolyl, isoindazolyl, benzopyranyl, coumarinyl, isocoumarinyl, quinolyl, isoquinolyl, napthridinyl, cinnolinyl, quinazolinyl, pyridopyridyl, benzoxazinyl, quinoxadinyl, chromenyl, chromanyl, isochromanyl, carbolinyl and the like. Also by way of example, $C_{5-30}$heterocyclyl is a cyclic aromatic or non-aromatic monovalent hydrocarbon radical having at least one heteroatom in the backbone of such cyclic hydrocarbon and having from 5 to 30 carbon atoms in the cyclic hydrocarbon.

As indicated in the definitions, the terms defined above may be used as part of a larger group.

For instance, as used herein, the term "(cycloalkyl)alkyl" refers to an alkyl group with a cycloalkyl substituent. Binding is through the alkyl group. Such groups have the number of carbon atoms as indicated. For example, $C_{4-30}$(cycloalkyl) alkyl refers to an alkyl group with a cycloalkyl substituent, where the total number of carbon atoms in the (cycloalkyl) alkyl group ranges between 4 and 30. Another example includes $C_{5-11}$cycloalkyl$C_{1-6}$alkyl and refers to a $C_{1-6}$alkyl group with a $C_{5-11}$cycloalkyl substituent.

As used herein, the term "(cycloalkenyl)alkyl" refers to an alkyl group with a cycloalkenyl substituent. Binding is through the alkyl group. Such groups have the number of carbon atoms as indicated. For example, $C_{4-30}$(cycloalkenyl) alkyl refers to an alkyl group with a cycloalkenyl substituent, where the total number of carbon atoms in the (cycloalkenyl) alkyl group ranges between 4 and 30. Another example includes $C_{5-11}$cycloalkenyl$C_{1-6}$alkyl and refers to a $C_{1-6}$alkyl group with a $C_{5-11}$cycloalkenyl substituent.

As used herein, the term "(cycloalkynyl)alkyl" refers to an alkyl group with a cycloalkynyl substituent. Binding is through the alkyl group. Such groups have the number of carbon atoms as indicated. For example, $C_{9-30}$(cycloalkynyl) alkyl refers to an alkyl group with a cycloalkynyl substituent, where the total number of carbon atoms in the (cycloalkynyl) alkyl group ranges between 9 and 30. Another example includes $C_{8-11}$cycloalkynyl$C_{1-6}$alkyl and refers to a $C_{1-6}$alkyl group with a $C_{8-11}$cycloalkynyl substituent.

As used herein, the term "alkoxyalkyl" refers to an alkyl group having an alkoxy (also named alkyloxy) substituent. Binding is through the alkyl group. The alkyl group and/or the alkoxy group has the number of carbon atoms as indicated. For example, $C_{2\text{-}20}$alkoxyalkyl refers to an alkyl group with a alkoxy substituent, where the total number of carbon atoms in the alkyloxyalkyl group ranges between 2 and 20. Another example includes $C_{1\text{-}6}$alkoxy$C_{1\text{-}6}$alkyl and refers to a $C_{1\text{-}6}$alkyl group with a $C_{1\text{-}6}$alkoxy substituent.

As used herein, the term "alkoxyaryl" refers to an aryl group having an alkoxy substituent. Binding is through the aryl group. The aryl group and/or the alkoxy group has the number of carbon atoms as indicated. For example, $C_{7\text{-}20}$alkoxyaryl refers to an aryl group with a alkoxy substituent, where the total number of carbon atoms in the alkyloxyaryl group ranges between 7 and 20. Another example includes $C_{1\text{-}6}$alkoxy-$C_{5\text{-}10}$aryl and refers to a $C_{5\text{-}10}$aryl group with a $C_{1\text{-}6}$alkoxy substituent.

As used herein, the term "alkylaryl" refers to an alkyl group with an aryl substituent. Binding is through the aryl group. Such groups have the number of carbon atoms as indicated. For example, $C_{7\text{-}30}$alkylaryl refers to an aryl group with a alkyl substituent, where the total number of carbon atoms in the alkylaryl group ranges between 7 and 30. Another example includes $C_{1\text{-}6}$alkyl$C_{5\text{-}11}$aryl and refers to a $C_{5\text{-}11}$aryl group with a $C_{1\text{-}6}$alkyl substituent.

As used herein, the term "arylalkyl" refers to an aryl group with an alkyl substituent. Binding is through the alkyl group. Such groups have the number of carbon atoms as indicated. For example, $C_{7\text{-}30}$arylalkyl refers to an alkyl group with a aryl substituent, where the total number of carbon atoms in the arylalkyl group ranges between 7 and 30. Another example includes $C_{5\text{-}11}$aryl$C_{1\text{-}6}$alkyl and refers to a $C_{1\text{-}6}$alkyl group with a $C_{5\text{-}11}$aryl substituent.

As used herein, the term "alkylheterocyclyl" refers to an alkyl group with an heterocyclyl substituent. Binding is through the heterocyclyl group. Such groups have the number of carbon atoms as indicated. For example, $C_{2\text{-}30}$alkylheterocyclyl refers to an heterocyclyl group with a alkyl substituent, where the total number of carbon atoms in the alkylheterocyclyl group ranges between 2 and 30. Another example includes $C_{1\text{-}6}$alkyl$C_{1\text{-}11}$heterocyclyl and refers to a $C_{1\text{-}11}$heterocyclyl group with a $C_{1\text{-}6}$alkyl substituent.

As used herein, the term "heterocyclylalkyl" refers to an heterocyclyl group with an alkyl substituent. Binding is through the alkyl group. Such groups have the number of carbon atoms as indicated. For example, $C_{2\text{-}30}$heterocyclylalkyl refers to an alkyl group with a heterocyclyl substituent, where the total number of carbon atoms in the heterocyclylalkyl group ranges between 2 and 30. Another example includes $C_{1\text{-}11}$heterocyclyl$C_{1\text{-}6}$alkyl and refers to a $C_{1\text{-}6}$alkyl group with a $C_{1\text{-}11}$heterocyclyl substituent.

As used herein, the term "bivalent hydrocarbon radicals" refers to any bivalent cyclic, heterocyclic, straight chain, branched chain, saturated or unsaturated radical, which contains a carbon backbone comprising one or more hydrogen atoms, optionally with one or more heteroatoms in the carbon backbone. The term "bivalent hydrocarbon radical" is intended to encompass the terms "alkanediyl", "alkenediyl", "alkynediyl", "cycloalkanediyl", "cycloalkenediyl" and "cycloalkynediyl".

The term "alkanediyl" is defined identically the same as "alkyl" but is bivalent instead of monovalent. The term "alkenediyl" is defined identically the same as "alkenyl" but is bivalent instead of monovalent. The term "alkynediyl" is defined identically the same as "alkynyl" but is bivalent instead of monovalent. The term "cycloalkanediyl" is defined identically the same as "cycloalkyl" but is bivalent instead of monovalent. The term "cycloalkenediyl" is defined identically the same as "alkenyl" but is bivalent instead of monovalent. The term "cycloalkynediyl" is defined identically the same as "alkynyl" but is bivalent instead of monovalent.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

As used herein, the term "heteroatom" includes N, O and S.

The compounds and their intermediates according to the present invention may occur in their base form or in a salt form. All salts, whether pharmaceutically acceptable or not are included within the ambit of the present invention.

The salt forms which the compounds and their intermediates according to the present invention are able to form can conveniently be prepared using the appropriate acids, such as, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic and the like acids; or using organic and inorganic bases to form base salt forms such as, for example, the ammonium salts, quaternary ammonium salts, the alkali and earth alkaline metal salts, e.g. the lithium, sodium, potassium, magnesium, calcium salts and the like, salts with organic bases, e.g. the benzathine, N-methyl, -D-glucamine, hydrabamine salts, and salts with amino acids such as, for example, arginine, lysine and the like.

Said acid addition salt forms can be converted by treatment with an appropriate base into the free base form. Conversely said base addition salt forms can be converted by treatment with an appropriate acid into the free acid form.

X and Y are preferably the same. X and Y are preferably C.

$R^1$, $R^2$, $R^3$ and $R^4$ are preferably independently selected from the group consisting of —H, $C_{1\text{-}20}$alkyl, $C_{2\text{-}20}$alkenyl, $C_{2\text{-}20}$alkoxyalkyl, $C_{7\text{-}20}$alkoxyaryl, $C_{2\text{-}20}$alkynyl, $C_{3\text{-}30}$cycloalkyl, $C_{4\text{-}30}$(cycloalkyl)alkyl, $C_{4\text{-}30}$(cycloalkenyl)alkyl, $C_{9\text{-}30}$(cycloalkynyl)alkyl, $C_{3\text{-}30}$cycloalkenyl, $C_{4\text{-}30}$cycloalkynyl, $C_{7\text{-}30}$arylalkyl, $C_{7\text{-}30}$alkylaryl, $C_{6\text{-}30}$aryl, $C_{6\text{-}30}$heterocyclylalkyl, $C_{6\text{-}30}$alkylheterocyclyl and $C_{5\text{-}30}$heterocyclyl.

$R^1$, $R^2$, $R^3$ and $R^4$ are preferably independently selected from the group consisting of —H, $C_{1\text{-}16}$alkyl, $C_{2\text{-}16}$alkenyl, $C_{2\text{-}16}$alkoxyalkyl, $C_{7\text{-}16}$alkoxyaryl, $C_{2\text{-}16}$alkynyl, $C_{3\text{-}20}$cycloalkyl, $C_{4\text{-}20}$(cycloalkyl)alkyl, $C_{4\text{-}20}$(cycloalkenyl)alkyl, $C_{9\text{-}20}$(cycloalkynyl)alkyl, $C_{3\text{-}20}$cycloalkenyl, $C_{4\text{-}20}$cycloalkynyl, $C_{7\text{-}20}$arylalkyl, $C_{7\text{-}20}$alkylaryl, $C_{6\text{-}20}$aryl, $C_{6\text{-}20}$heterocyclylalkyl, $C_{6\text{-}20}$alkylheterocyclyl and $C_{5\text{-}20}$heterocyclyl.

$R^1$, $R^2$, $R^3$ and $R^4$ are preferably independently selected from the group consisting of —H, primary or secondary $C_{1\text{-}6}$alkyl, $C_{2\text{-}6}$alkenyl, $C_{1\text{-}6}$alkoxy$C_{1\text{-}6}$alkyl, $C_{1\text{-}6}$alkoxy-$C_{5\text{-}10}$aryl, $C_{5\text{-}7}$cycloalkyl, $C_{5\text{-}11}$cycloalkyl$C_{1\text{-}6}$alkyl, $C_{4\text{-}11}$cycloalkenyl$C_{1\text{-}6}$alkyl, $C_{8\text{-}12}$cycloalkynyl$C_{1\text{-}6}$alkyl, $C_{5\text{-}7}$cycloalkenyl, $C_{5\text{-}7}$cycloalkynyl, $C_{6\text{-}11}$aryl$C_{1\text{-}6}$alkyl, $C_{1-6}$alkyl$C_{6-11}$aryl, $C_{6-11}$aryl, $C_{5-12}$heterocyclyl$C_{1-6}$alkyl, $C_{1-6}$alkyl$C_{5-12}$heterocyclyl and $C_{5-12}$heterocyclyl.

Preferably, $R^1$, $R^2$, $R^3$ and $R^4$ are other than —H.

Preferably $R^1$, $R^2$, $R^3$ and $R^4$ are independently selected from the group consisting of —H, methyl, ethyl, propyl, butyl, hexyl, cyclohexyl, octyl, nonyl, dodecyl, eicosyl, norbornyl, adamantyl, vinyl, propenyl, cyclohexenyl, phenylethyl, phenylpropyl, methoxyphenyl, ethoxyphenyl, phenyl, tolyl, dimethylphenyl, trimethylphenyl, ethylphenyl, propylphenyl, biphenyl, naphthyl, methylnaphthyl, anthryl, phenanthryl, benzylphenyl, pyrenyl, tetrahydropyranyl, acenaphthyl, phenalenyl, aceanthrylenyl, tetrahydronaphthyl, indanyl, methoxypropyl, ethoxyethyl, methoxymethyl, amyl, trityl, methoxytrityl, dimethoxytrityl, trimethoxytrityl, allyl, trimethylsilyl, (t-butyl)-dimethylsilyl, and benzyl, including isomers thereof.

Preferably $R^1$, $R^2$, $R^3$ and $R^4$ are selected from the group consisting of methyl, ethyl, n-propyl, s-propyl, n-butyl, s-butyl, t-butyl, benzyl, phenyl and methoxyphenyl.

Preferably $R^1$ and $R^2$ are the same. Preferably $R^3$ and $R^4$ are the same.

Preferably $R^1$, $R^2$, $R^3$ and $R^4$ are the same and are selected from the group consisting of methyl, ethyl, n-propyl, s-propyl and t-butyl.

Preferably $R^1$, $R^2$, $R^3$ and $R^4$ are all ethyl.

Preferably $R^1$ and $R^2$ are taken together to form —$R^1$-$R^2$— and $R^3$ and $R^4$ are taken together to form —$R^3$-$R^4$—.

Preferably $R^1$ and $R^2$ are taken together to form —$R^1$-$R^2$— and $R^3$ and $R^4$ are taken together to form —$R^3$-$R^4$—, and —$R^1$-$R^2$— and —$R^3$-$R^4$— each independently is $C_{1-20}$alkanediyl, $C_{2-20}$alkenediyl, $C_{4-20}$alkynediyl, $C_{3-20}$cycloalkanediyl, $C_{4-20}$cycloalkenediyl and $C_{8-20}$cycloalkynediyl.

Preferably $R^1$ and $R^2$ are taken together to form —$R^1$-$R^2$— and $R^3$ and $R^4$ are taken together to form —$R^3$-$R^4$—, and —$R^1$-$R^2$— and —$R^3$-$R^4$— are the same and are selected from the group consisting of $C_{1-20}$alkanediyl, $C_{2-20}$alkenediyl, $C_{4-20}$alkynediyl, $C_{3-20}$cycloalkanediyl, $C_{4-20}$cycloalkenediyl and $C_{8-20}$cycloalkynediyl.

Preferably X and Y are the same, and $R^1$, $R^2$, $R^3$ and $R^4$ are the same.

Preferably X and Y are C and $R^1$, $R^2$, $R^3$ and $R^4$ are the same.

Preferably X and Y are C and $R^1$, $R^2$, $R^3$ and $R^4$ are the same and are selected from the group consisting of $C_{1-20}$alkyl, $C_{2-20}$alkenyl, $C_{2-20}$alkoxyalkyl, $C_{7-20}$alkoxyaryl, $C_{2-20}$alkynyl, $C_{3-30}$cycloalkyl, $C_{4-30}$(cycloalkyl)alkyl, $C_{3-30}$cycloalkenyl, $C_{4-30}$cycloalkynyl, $C_{7-30}$arylalkyl, $C_{7-30}$alkylaryl, $C_{6-30}$aryl, $C_{6-30}$heterocyclylalkyl, $C_{6-30}$alkheterocyclyl and $C_{5-30}$heterocyclyl.

Preferably X and Y are C and $R^1$, $R^2$, $R^3$ and $R^4$ are the same and are selected from the group consisting of $C_{1-16}$alkyl, $C_{2-16}$alkenyl, $C_{2-16}$alkoxyalkyl, $C_{7-16}$alkoxyaryl, $C_{2-16}$alkynyl, $C_{3-20}$cycloalkyl, $C_{4-20}$(cycloalkyl)alkyl, $C_{3-20}$cycloalkenyl, $C_{4-20}$cycloalkynyl, $C_{7-20}$arylalkyl, $C_{7-20}$alkylaryl, $C_{6-20}$aryl, $C_{6-20}$heterocyclylalkyl, $C_{6-20}$alkheterocyclyl and $C_{5-20}$heterocyclyl.

Preferably X and Y are C and $R^1$, $R^2$, $R^3$ and $R^4$ are the same and are selected from the group consisting of primary or secondary $C_{1-6}$alkyl, $C_{2-6}$alkenyl, $C_{1-6}$alkoxy$C_{1-6}$alkyl, $C_{1-6}$alkoxy$C_{5-10}$aryl, $C_{5-7}$cycloalkyl, $C_{5-11}$cycloalkyl$C_{1-6}$alkyl, $C_{5-7}$cycloalkenyl, $C_{5-7}$cycloalkynyl, $C_{6-11}$aryl$C_{1-6}$alkyl, $C_{1-6}$alkyl$C_{6-11}$aryl, $C_{6-11}$aryl, $C_{5-12}$heterocyclyl$C_{1-6}$alkyl, $C_{1-6}$alkyl$C_{5-12}$heterocyclyl and $C_{5-12}$heterocyclyl.

Preferably X and Y are C and $R^1$, $R^2$, $R^3$ and $R^4$ are the same and are selected from the group consisting of methyl, ethyl, propyl, butyl, hexyl, cyclohexyl, octyl, nonyl, dodecyl, eicosyl, norbornyl, adamantyl, vinyl, propenyl, cyclohexenyl, phenylethyl, phenylpropyl, methoxyphenyl, ethoxyphenyl, phenyl, tolyl, dimethylphenyl, trimethylphenyl, ethylphenyl, propylphenyl, biphenyl, naphthyl, methylnaphthyl, anthryl, phenanthryl, benzylphenyl, pyrenyl, tetrahydropyranyl, acenaphthyl, phenalenyl, aceanthrylenyl, tetrahydronaphthyl, indanyl, methoxypropyl, ethoxyethyl, methoxymethyl, amyl, trityl, methoxytrityl, dimethoxytrityl, trimethoxytrityl, allyl, trimethylsilyl, (t-butyl)dimethylsilyl, and benzyl, including isomers thereof.

Preferably X and Y are C and $R^1$, $R^2$, $R^3$ and $R^4$ are the same and are selected from the group consisting of methyl, ethyl, n-propyl, s-propyl, n-butyl, s-butyl, t-butyl, benzyl, phenyl and methoxyphenyl.

Preferably X and Y are C and $R^1$, $R^2$, $R^3$ and $R^4$ are the same and are selected from the group consisting of methyl, ethyl, n-propyl, s-propyl and t-butyl.

Preferably $R^1$, $R^2$, $R^3$ and $R^4$ are ethyl.

Preferably X and Y are C and $R^1$ and $R^2$ are taken together to form —$R^1$-$R^2$— and $R^3$ and $R^4$ are taken together to form —$R^3$-$R^4$—, and —$R^1$-$R^2$— and —$R^3$-$R^4$— are the same and are selected from the group consisting of $C_{1-20}$alkanediyl, $C_{2-20}$alkenediyl, $C_{4-20}$alkynediyl, $C_{3-20}$cycloalkanediyl, $C_{4-20}$cycloalkenediyl and $C_{8-20}$cycloalkynediyl.

Where X or Y is Si, $R^1$, $R^2$, $R^3$ and $R^4$ are preferably $C_{1-20}$alkyl, more preferably $C_{1-6}$alkyl, even more preferably t-butyl.

For purposes of denoting the stereochemistry of the compounds of formula (I), the following numbering of the bicyclic ring system is used throughout the text.

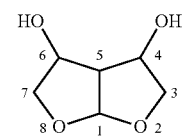

Compound (I) is intended to encompass all preferably thermodynamically stable stereoisomers thereof. Stereoisomers with a cis configuration are those stereoisomers that have the hydrogen atom on carbon 5 and the hydrogen atom on carbon 1 on the same side of the ringsystem formed by the two tetrahydrofuran rings. Stereoisomers with a trans configuration are those stereoisomers that have the hydrogen atom on carbon 5 and the hydrogen atom on carbon 1 on the opposite side of the ringsystem formed by the two tetrahydrofuran rings. Stereoisomers having a cis configuration are preferred. Based on the preparation of the compounds of formula (I) under thermodynamic reaction conditions and the X-ray analysis thereof, it was observed that stereoisomers having the trans configuration are thermodynamically less stable than the cis stereoisomers. In particular, stereoisomers (Ia), (Ib), (Ic) and (Id) are preferred.

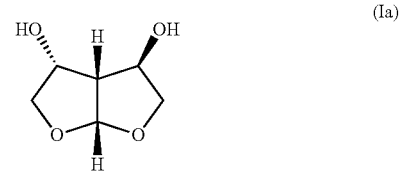

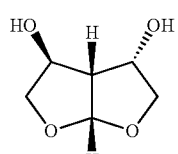
(Ib)

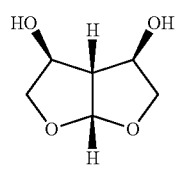
(Ic)

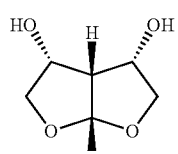
(Id)

Compounds of formula (Ia) and (Ib) have an enantiomeric relationship. Compounds of formula (Ic) and (Id) have a diastereomeric relationship. Compounds of formula (Ic) and (Ia) have a diastereomeric relationship. Compounds of formula (Ic) and (Ib) have a diastereomeric relationship. Compounds of formula (Ia) and (Id) have a diastereomeric relationship. Compounds of formula (Ib) and (Id) have a diastereomeric relationship.

A compound having formula (II) is intended to encompass all stereoisomers thereof. Depending on the nature of X, Y, $R^1$, $R^2$, $R^3$ and $R^4$, the stereogenicity of the central carbon atom bearing the aldehyde moiety may be different. In particular, the stereoisomers used in the preparation of the compounds of formula (Ia), (Ib), (Ic) and (Id) are preferred, i.e. compound of formula (Ia) is prepared from compound (IIa), compound (IIb) is needed for preparing compound (Ib), a mixture of compound (IIc) and compound (IId) will lead to a mixture of compounds (Ic) and (Id) in which compound (IIc) can lead to the formation of compound (Ic) and compound (Id) and compound (IId) can lead to the formation of compound (Ic) and compound (Id).

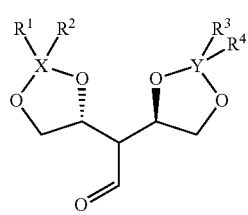
(IIa)

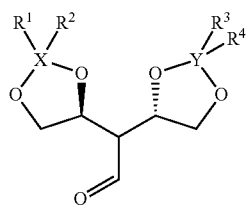
(IIb)

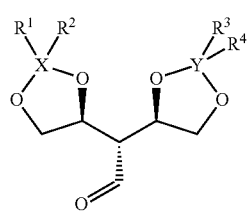
(IIc)

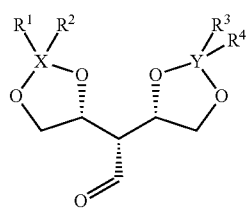
(IId)

A compound having formula (III) is intended to encompass all stereoisomers thereof. Depending on the nature of X, Y, $R^1$, $R^2$, $R^3$ and $R^4$, the stereogenicity of the central carbon atom bearing the hydroxyalkyl moiety may be different. In particular, the stereoisomers used in the preparation of the compounds of formula (Ia), (Ib), (Ic) and (Id) are preferred, i.e. compound of formula (Ia) is ultimately prepared from compound (IIIa), compound (IIIb) is needed for ultimately preparing compound (Ib), a mixture of compound (IIIc) and compound (IIId) will ultimately lead to a mixture of compounds (Ic) and (Id) in which compound (IIIc) ultimately leads to the formation of compound (Ic) and compound (IIId) ultimately leads to the formation of (Id).

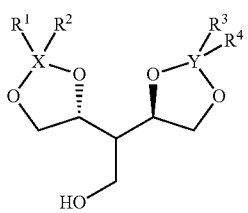
(IIIa)

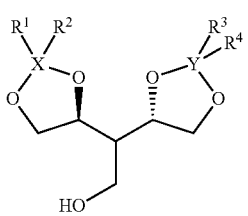
(IIIb)

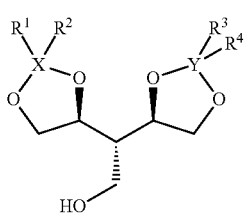
(IIIc)

(IIId)

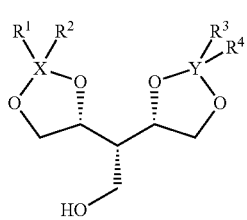

A compound having formula (IV) is intended to encompass all stereoisomers thereof. In particular, the stereoisomers used in the preparation of the compounds of formula (Ia), (Ib), (Ic) and (Id) are preferred, i.e. compound of formula (Ia) is ultimately prepared from compound (IVa), compound (IVb) is needed for ultimately preparing compound (Ib), a mixture of compound (IVc) and compound (IVd) will ultimately lead to a mixture of compounds (Ic) and (Id).

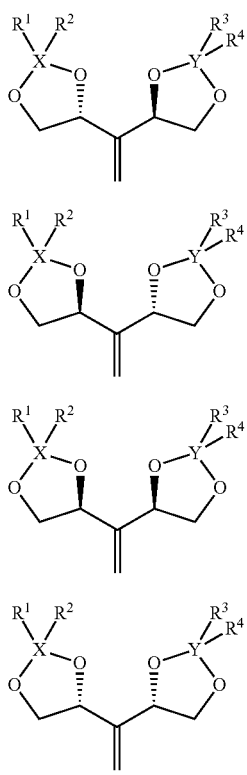

Interesting compounds having formula (II) are those compounds of formula (II) wherein $XR^1R^2$ and $YR^3R^4$ are identical. Also interesting compounds having formula (II) are those compounds of formula (II) wherein X and Y are C and $R^1$, $R^2$, $R^3$ and $R^4$ are identical. Other interesting compounds having formula (II) are those compounds of formula (II) wherein X and Y are C and $R^1$, $R^2$, $R^3$ and $R^4$ are $C_{1-20}$alkyl. Yet other interesting compounds having formula (II) are those compounds of formula (II) wherein X and Y are C and $R^1$, $R^2$, $R^3$ and $R^4$ are ethyl.

Interesting compounds having formula (III) are those compounds of formula (III) wherein $XR^1R^2$ and $YR^3R^4$ are identical. Also interesting compounds having formula (III) are those compounds of formula (III) wherein X and Y are C and $R^1$, $R^2$, $R^3$ and $R^4$ are identical. Other interesting compounds having formula (III) are those compounds of formula (III) wherein X and Y are C and $R^1$, $R^2$, $R^3$ and $R^4$ are $C_{1-20}$alkyl. Yet other interesting compounds having formula (III) are those compounds of formula (III) wherein X and Y are C and $R^1$, $R^2$, $R^3$ and $R^4$ are ethyl.

Interesting compounds having formula (IV) are those compounds of formula (IV) wherein $XR^1R^2$ and $YR^3R^4$ are identical. Also interesting compounds having formula (IV) are those compounds of formula (IV) wherein X and Y are C and $R^1$, $R^2$, $R^3$ and $R^4$ are identical. Other interesting compounds having formula (IV) are those compounds of formula (IV) wherein X and Y are C and $R^1$, $R^2$, $R^3$ and $R^4$ are $C_{1-20}$alkyl. Yet other interesting compounds having formula (IV) are those compounds of formula (IV) wherein X and Y are C and $R^1$, $R^2$, $R^3$ and $R^4$ are ethyl.

In general, the compounds of formula (I) can be prepared according to reaction scheme A.

Scheme A

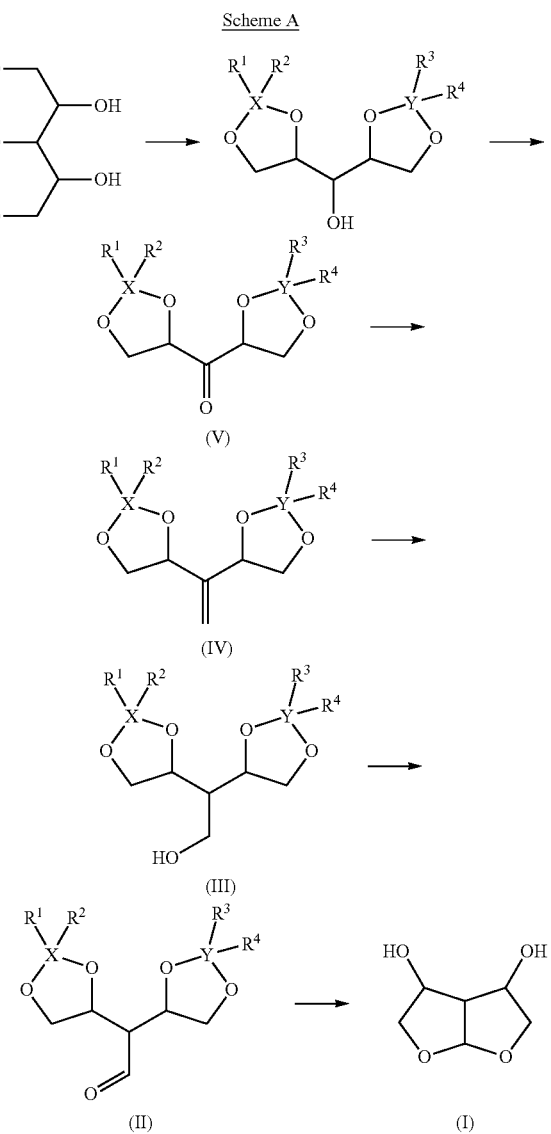

Suitable deprotecting agents used in the deprotection and subsequent intramolecular cyclisation of compounds having formula (II) to compounds having formula (I) are selected from hydrogenolysis reagents, fluoride reagents, acids and bases, preferably, inorganic and organic acids, most preferably sulfonic acids or carboxylic acids.

Suitable acids are selected from the group consisting of hydrochloric acid, hydrobromic acid, sulfuric acid, phosphoric acid, nitric acid, formic acid, acetic acid, propionic acid, succinic acid, glycollic acid, lactic acid, malic acid, tartaric acid, trifluoroacetic acid, gluconic acid, citric acid, maleic acid, fumaric acid, pyruvic acid, phenylacetic acid, benzoic acid, 4-aminobenzoic acid, anthranilic acid, 4-hydroxybenzoic acid, salicylic acid, 4-aminosalicylic acid, pamoic acid, nicotinic acid, methanesulfonic acid, ethanesulfonic acid, hydroxyethanesulfonic acid, benzenesulfonic acid, p-toluene-sulfonic acid, naphthalenesulfonic acid, sulfanilic acid, cyclohexylsulfamic acid, camphorsulfonic acid, chlorosulfonic acid, pyridinium para toluenesulfonic acid and ascorbic acid.

The deprotection and subsequent intramolecular cyclisation of compounds having formula (II) preferably takes place in an aqueous solution. Preferably, the aqueous solution comprises one or more organic solvents. A preferred organic solvent is dichloromethane. Other suitable organic solvents can be selected from the group consisting of alcohols, preferably $C_1$-$C_{10}$ alcohols. Preferred alcohols are selected from a group consisting of methanol, ethanol, propanol, butanol, pentanol, hexanol and isomers thereof. Mixtures of one or more solvents may be used.

The deprotection and subsequent intramolecular cyclisation preferably takes place at a temperature of 0° C. to 100° C., preferably 10° C. to 50° C., preferably at about 25° C.

Deprotection and subsequent intramolecular cyclisation is usually effected in 10 minutes to 4 days depending on the reaction conditions. Under the preferred conditions indicated above, the deprotection and subsequent intramolecular cyclisation is substantially complete after about 15 minutes.

Oxidizing agents used in the oxidation of a compound having formula (III) to a compound having formula (II) include any oxidizing agent capable of converting a primary alcohol to an aldehyde.

Preferred oxidizing methods used in the oxidation of compounds having formula (III) to compounds having formula (II) include dimethylsulfoxide-mediated oxidation. Dimethylsulfoxide (DMSO) can be activated by reaction with a variety of electrophilic reagents, including oxalyl chloride, dicyclohexylcarbodiimide, sulfur trioxide, acetic anhydride, and N-chlorosuccinimide. A number of reviews of dimethylsulfoxide-mediated oxidation are reported (Lee, *Comprehensive Organic Synthesis*, Trost, B. M.; Fleming, I., Eds., Pergamon Press: New York, 1991, Vol. 7, p. 291-303. Tidwell, T. T. *Synthesis* 1990, 857-870. Tidwell, T. T. *Organic Reactions* 1990, 39, 297-557.

Oxidations of compounds having formula (III) to compounds having formula (II) are preferably carried out using Swern, Pfitzner-Moffatt or Parikh-Doering conditions, most preferably Parikh-Doering conditions.

The Parikh-Doering reaction includes the activation of dimethylsulfoxide with a sulfur trioxide-pyridine complex and is described by Parikh, J. P.; Doering, W. E. *J. Am. Chem. Soc.*, 1967, 89, 5505-5507.

Swern oxidation involves the activation of dimethylsulfoxide using triethylamine and oxalylchloride or trifluoroacetic anhydride. The Swern oxidation is reported by A. J. Mancuso, D. Swern, *Synthesis* 1981, 165-185.

Pfitzner-Moffatt Oxidation involves the activation of dimethyl sulfoxide by a dialkylcarboimide reagent such as dicyclohexyl, diisopropyl; and is described by K. E. Pfitzner, J. G. Moffatt, *J. Am. Chem. Soc.* 85, 3027 (1963).

Dimethylsulfoxide-mediated oxidation allows the reaction to be easily controlled and the alcohols to be oxidized to the corresponding aldehydes in high yields since the aldehydes produced are prevented from the further oxidation to the corresponding carboxylic acid.

The oxidation of compounds having formula (III) to compounds having formula (II) is preferably carried out in an organic solvent, preferably a reaction-inert solvent. Suitable solvents are selected from the group consisting of hydrocarbons, chlorinated hydrocarbons, ketones, polar aprotic solvents, aromatic hydrocarbons, and mixtures thereof.

Preferred reaction-inert solvents are selected from the group consisting of pentane, hexane, heptane, cyclohexane, dichloromethane 1,2-dichloroethane, 1,1,2,2-tetra-chloroethane, acetone, methyl ethyl ketone, acetonitrile, propionitrile, benzene, toluene, chlorobenzene, xylene, ether, 1,4-dioxane, tetrahydrofuran and mixtures thereof.

Oxidation of compounds having formula (III) to compounds having formula (II) preferably takes place at a temperature in the range of −50° C. to 50° C., preferably lower than 25° C., most preferably in the range −10° C. to 5° C.

Oxidation of compounds having formula (III) to compounds having formula (II) preferably takes place in 10 minutes to 2 days depending on the reaction conditions. Under the preferred conditions indicated above, the oxidation reaction is substantially complete after about 4 hours. Under the most preferred conditions mentioned above, the oxidation reaction is substantially completed after about 1.5 hours.

Hydroboration and subsequent oxidation of the compounds having formula (IV) may be carried out under any conditions capable of converting the alkene to the primary alcohol of (III).

Preferred conditions include reaction of compounds having formula (IV) with a suitable boron-containing reagent and subsequent reaction using an oxidising agent.

Suitable boron-containing reagents for the hydroboration of compounds having formula (IV) are selected from the group consisting of $BH_3$, $C_1$-$C_6$ mono- or dialkylboranes, $C_6$-$C_{18}$ bicycloalkylboranes, $C_6$-$C_{18}$ arylboranes and mixtures thereof. Preferred hydroboration reagents are selected from the group consisting of $BH_3$, dimethylborane, diethylborane, dipropylborane, 9-borabicyclo[3.3.1]nonane[9-BBN], catecholborane, pinylborane, borolane, and mixtures thereof.

A preferred boron-containing reagent includes diethylborane which may be prepared in situ by combining $BH_3$ and triethylborane.

The reaction of compounds having formula (IV) with the boron-containing reagent(s) preferably takes place in the presence of a solvent. Suitable solvents selected from the group consisting of aromatic hydrocarbons and ethers. Preferred solvents are selected from the group consisting of benzene, toluene, xylene, ether, 1,4-dioxane, tetrahydrofuran and mixtures thereof. Tetrahydrofuran is particularly preferred.

The reaction of compounds having formula (IV) with the boron-containing reagent(s) preferably takes place at a temperature in the range of 0° C. to 50° C., preferably about 25° C.

The reaction of compounds having formula (IV) with the boron-containing reagent(s) preferably takes place in 5 minutes to 1 day depending on the reaction conditions. Under the preferred conditions indicated above, the reaction is substantially complete after about 1 hour.

Following the reaction of compounds having formula (IV) with the boron-containing reagent(s), the reaction products are usually converted to the alcohol in the presence of an oxidising agent. Suitable oxidising agents include peroxides, particularly hydrogen peroxide. Oxidation preferably takes place in an aqueous basic solution. Suitable basic materials include alkali metal carbonates and alkyl metal hydroxides. Sodium hydroxide is a particularly preferred base.

The oxidation part of the hydroboration reaction preferably takes place at a temperature in the range of −20° C. to 30° C., preferably about 0° C.

The oxidation part of the hydroboration reaction preferably takes place in 5 minutes to 1 day depending on the reaction conditions. Under the preferred conditions indicated above, the oxidation reaction is substantially complete after about 2 hours.

The Wittig type reaction carried out on compounds having formula (V) to produce compounds having formula (IV) may be effected by a classical Wittig reaction or a modified Wittig reaction such as the Horner-Emmons reaction or the Wittig-Horner reaction.

Preferred reagents for the classical Wittig reaction include phosphonium ylides, which may be prepared by combining a phosphonium salt with a base. Phosphonium salts may be obtained from for instance a triarylphosphine with a halomethane. Tri-$C_6$-$C_{20}$arylphosphines are preferred, particularly triphenylphosphine. The halomethane is preferably bromomethane or chloromethane. The base is preferably an organo-alkali metal reagent such as sodium or lithium hexamethyldisilazane.

The Wittig reaction to convert compounds having formula (V) to compounds having formula (IV) is preferably carried out in an organic solvent, preferably a reaction-inert solvent. Suitable solvents are selected from the group consisting of hydrocarbons, chlorinated hydrocarbons, ethers, polar aprotic solvents, aromatic hydrocarbons, and mixtures thereof. A preferred solvent is tetrahydrofuran.

The Wittig type reaction of compounds having formula (V) to compounds having formula (IV) preferably takes place at a temperature in the range of −50° C. to 20° C., preferably lower than 25° C., most preferably in the range −10° C. to 5° C.

Other Wittig-type reagents instead of phosphonium ylidess include phosphonic acid derivatives, Tebbe reagent or Petasis reagent and may be used according to art-known reaction conditions.

The compounds of formula (IV) may be prepared using a process identical or analogous to the processes described in Maleczka et al., Org Lett 2002, 4(17), 2841-2844.

The compounds of formula (V) may be prepared using a process identical or analogous to the processes described in Linclau et al (*J. Org. Chem.* 2003, 68, 1821-1826).

All of the above-described processes may take place separately or as a series of reactions.

Pure stereoisomeric forms of the compounds as mentioned herein are defined as isomers substantially free of other enantiomeric or diastereomeric forms of the same basic molecular structure of said compounds. In particular, the term 'stereoisomerically pure' concerns compounds having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds having a stereoisomeric excess of 90% up to 100%, even more in particular having a stereoisomeric excess of 94% up to 100% and most in particular having a stereoisomeric excess of 97% up to 100%. The terms 'enantiomerically pure' and 'diastereomerically pure' should be understood in a similar way, but then having regard to the enantiomeric excess, respectively the diastereomeric excess of the mixture in question.

In the event a reaction procedure results in a mixture of enantiomers, the enantiomers may be separated from each other by the selective crystallization of their diastereomeric salts with optically active acids or bases. Examples thereof are tartaric acid, dibenzoyltartaric acid, ditoluoyltartaric acid and camphosulfonic acid. Alternatively, enantiomers may be separated by chromatographic techniques using chiral stationary phases. Pure diastereomers from a diastereomeric mixture can be obtained by conventional methods. Appropriate physical separation methods that may advantageously be employed are, for example, selective crystallization and chromatography, e.g. column chromatography.

Pure stereochemically isomeric forms of the compounds of formula (I) may also be derived from the corresponding pure stereochemically isomeric forms of the appropriate starting materials, provided that the reaction occurs stereospecifically.

For instance, a compound of formula (Ia) can be prepared starting from pure L-arabitol and is depicted in scheme B. A compound of formula (Ib) can be prepared starting from pure D-arabitol. Using xylitol or ribitol (or adonitol) as starting material will lead to a mixture of diastereoisomers of formula (Ic) and (Id), which mixture may be separated using art-known separation techniques.

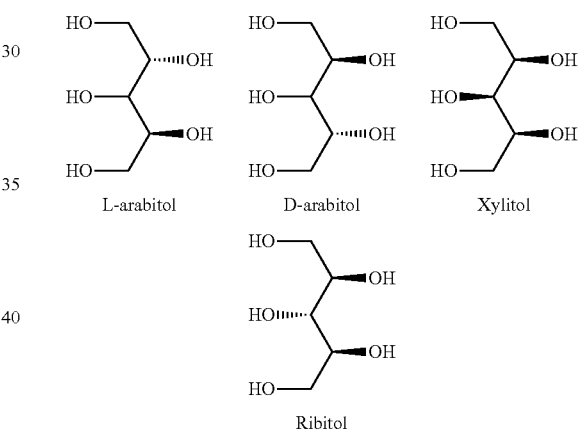

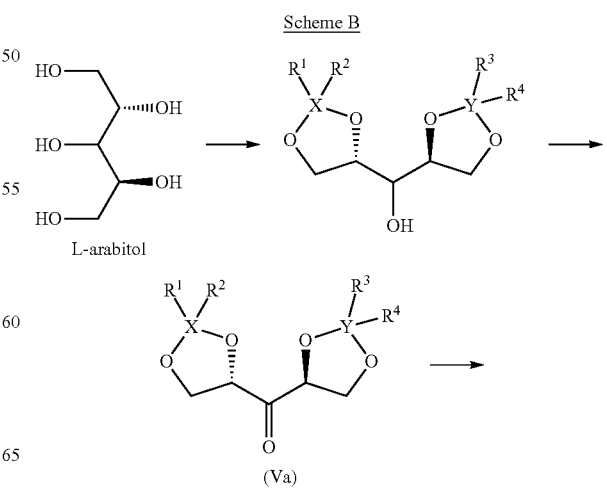

Scheme B

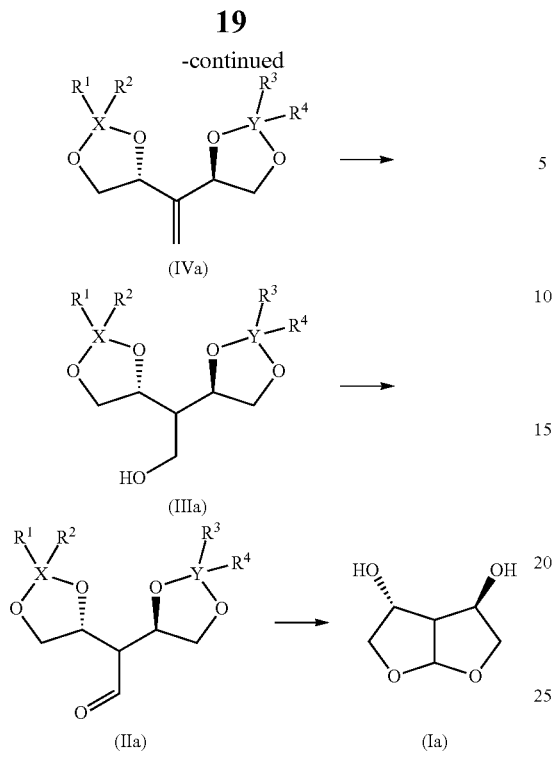

(IVa)

(IIIa)

(IIa)    (Ia)

The compounds of formula (I) may be used to synthesize new HIV protease inhibitor drug candidates according to art-known synthesis procedures. Thus, the present invention also relates to the use of the compounds of formula (I) in the production of HIV protease inhibitors and the invention also relates to HIV protease inhibitors obtained by using a compound of formula (I) in the chemical preparation of said HIV protease inhibitors which show an antiviral activity against HIV wild type and/or HIV mutants resistant to currently available drugs.

The following examples illustrate the preparation specific compounds of the invention.

EXAMPLES

Preferably, synthesis of a compound (I) comprises a multi-step synthesis, one synthetic route to which is generally described below. The first two steps are described in detail by Linclau et al (*J. Org. Chem.* 2003, 68, 1821-1826). Accordingly, the first two steps described below are merely for reference. The synthesis suitably starts with the regioselective protection of arabitol, xylitol or ribitol, preferably arabitol. Arabitol has pseudo-C2-symmetry (central carbon is not stereogenic), and this symmetry is preserved in 1. While arabitol is chiral, xylitol and ribitol are meso-forms. In the second step, oxidation of protected arabitol leads to the C2-symmetric (2S,4S)-1,2:4,5-bis(3,3-pentylidenedioxy)-3-pentanone. Preferably a low temperature is used for this step as this minimises epimerisation to (2S,4R)-1,2:4,5-bis(3,3-pentylidenedioxy)-3-pentanone.

The terms used below are as follows:

| DCM | Dichloromethane |
| THF | Tetrahydrofuran |
| Ph | Phenyl |
| Py | Pyridine |
| DMSO | Dimethylsulfoxide |
| min | Minute |
| h | Hour |
| d | Day |
| Me | Methyl |
| Et | Ethyl |
| CSA | Chlorosulfonic acid |
| PPTS | Pyridinium para toluene sulfonic acid |
| NaHMDS | sodium hexamethyldisilazane |

Synthesis of cis-(4R,6R)-2,8-dioxa-4,6-dihydroxy bicyclo[3.3.0]octane

Step 1: Synthesis of (2S,4S)-1,2:4,5-Di-O-(3,3-pentylidene)arabitol

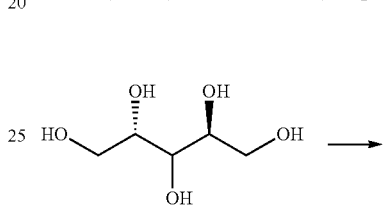

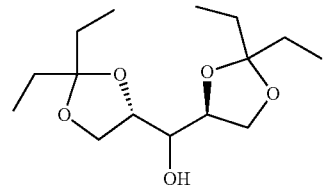

A refluxing suspension of L-arabitol (20.00 g, 131.5 mmol) and 3,3-dimethoxypentane (76.46 g, 578.4 mmol) in THF (200 mL) was stirred for 15 min. CSA (9.16 g, 39.4 mmol) was added and the reaction mixture was stirred at reflux for exactly 5 min. The reaction was quenched by addition of NaOH (aq, 2 M, 40 mL) at reflux. Diethylether (50 mL) and water (20 mL) were added and the layers separated. The aqueous phase was extracted with diethylether (3×50 mL). The combined organic layers were dried over anhydrous $Na_2SO_4$, filtered and the solvent removed in vacuo to give a pale yellow oil. The crude product was dissolved in $CH_2Cl_2$ (200 mL) and triethylamine (20 mL) was added. The mixture was heated under reflux and succinic anhydride (3.40 g, 34.0 mmol) was added. The reaction mixture was heated under reflux for 1.5 h, and then quenched with $NaHCO_3$ (aq, sat, 200 mL) at reflux temperature. After cooling the layers were separated and the aqueous layer extracted with $CH_2Cl_2$ (2×100 mL). The combined organic phases were washed with brine (100 mL), dried over anhydrous $Na_2SO_4$, filtered and evaporated to give a pale yellow oil. Purification by column chromatography (hexane/acetone 80:20) gave (2S,4S)-1,2:4,5-di-O-(3,3-pentylidene)arabitol as a pale yellow oil (28.18 g, 74%). $[\alpha]_D$ −5.8 (c 2.50, $CHCl_3$, 25° C.). The $^1H$ and $^{13}C$

Step 2: Synthesis of (2S,4S)-1,2:4,5-Bis(3,3-pentyl-idenedioxy)-3-pentanone

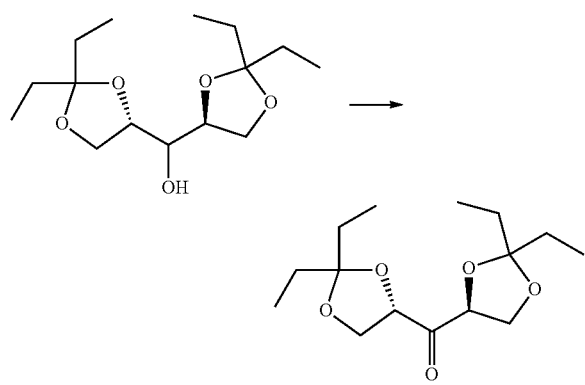

In a 500 mL 2 neck round-bottomed flask (A), was stirred a solution of the 1,2:4,5-di-O-isopentylidene acetal (10.00 g, 34.7 mmol) in CH$_2$Cl$_2$ (100 mL) and DMSO (50 mL) at 0° C. In a 250 mL 2 neck round-bottomed flask (B) was stirred a solution of SO$_3$.pyridine complex (16.56 g, 104.0 mmol), and triethylamine (17.9 mL, 128.3 mmol) in CH$_2$Cl$_2$ (50 mL) and DMSO (50 mL) at 0° C. for 10 min. The contents of flask (B) were then transferred via cannula to flask (A) over a period of 10 min. The reaction mixture was then stirred at 0° C. for 5 h. The reaction mixture was poured into a mixture of saturated aqueous NH$_4$Cl:water:diethylether:pentane (1:1:1:1, 600 mL). The layers were separated, and the aqueous layer extracted with a diethylether:pentane mixture (1:1, 2×150 mL). The combined organic phases were dried over anhydrous Na$_2$SO$_4$, filtered and evaporated to give the crude product as a pale yellow oil. Purification by column chromatography (hexane/ethyl acetate 90:10) gave (2S,4S)-1,2:4,5-bis(3,3-pentylidenedioxy)-3-pentanone as a colourless oil (9.20 g, 93%). [α]$_D$ −68.9 (c 0.31, CHCl$_3$, 25° C.). The $^1$H and $^{13}$C NMR spectra corresponded to the reported data in Linclau B. et al., J. Org. Chem. 2003, 68, 1821.

Step 3: synthesis of (2R,4R)-Di-O-(3,3-pentylidene)-3-deoxy-3-methylenearabitol

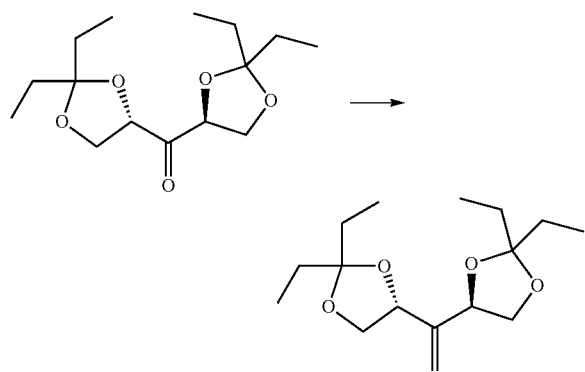

To a stirred suspension of methyltriphenylphosphonium bromide (21.20 g, 59.36 mmol) in THF (100 mL) at 0° C. was added NaHMDS (56.4 mL, 56.4 mmol, 1.0 M in THF). The resulting yellow suspension was stirred for 10 min. A solution of the C2-symmetric ketone (8.50 g, 29.7 mmol) dissolved in THF (20 mL) was then added dropwise and the mixture stirred at 0° C. for 4 h. The reaction mixture was poured into water (150 mL) and extracted with CH$_2$Cl$_2$ (3×100 mL). The combined organic phases were then dried over anhydrous Na$_2$SO$_4$, filtered and evaporated. Purification by column chromatography (hexane/ethylacetate 90:10) gave (2R,4R)-di-O-(3,3-pentylidene)-3-deoxy-3-methylenearabitol as a colourless oil (8.30 mg, 98%) (Maleczka et al. Organic Letters, (2002), 4(17), 2841-2844). R$_f$ 0.16 (hexane/ethylacetate 95:5). [α]$_D$ −86.9 (c 1.33, CHCl$_3$, 25° C.). $^1$H NMR (400 MHz, CDCl3) δ 5.30 (2H, d, J=1.0 Hz), 4.52 (2H, m), 4.19 (2H, dd, J=8.0, 6.0 Hz), 3.56 (2H, t, J=8.0 Hz), 1.74-1.60 (8H, m), 0.92 (6H, t, J=7.5 Hz), and 0.90 (6H, t, J=7.5 Hz).

Step 4: Synthesis of (2R,4R)-Di-O-(3,3-pentyl-idene)-3-deoxy-3-hydroxymethylarabitol

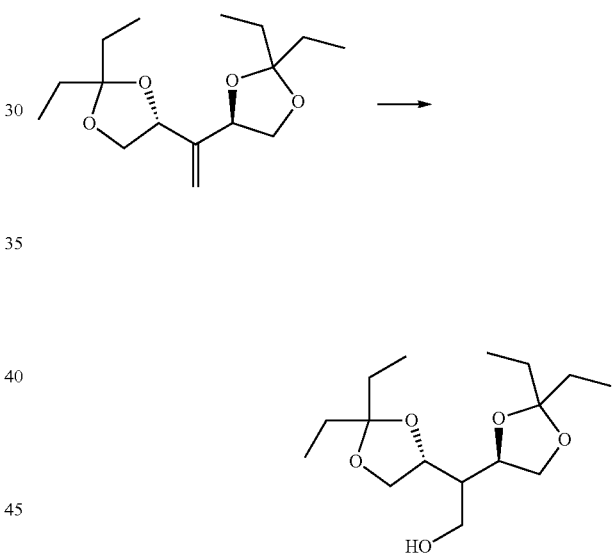

A solution of triethylborane (10.2 mL, 1.0 M in THF) and borane (1.7 mL, 1.0 M in THF) was stirred at room temperature for 1 h. A solution of the C2-symmetric alkene (968 mg, 3.40 mmol) in THF (7 mL) was added and the reaction mixture stirred for 2 d. The reaction mixture was then carefully pipetted dropwise into a stirred mixture of NaOH (aq, 3 M):H$_2$O$_2$ (aq, 27% wt.):CH$_2$Cl$_2$ (1:1:1, 90 mL) at 0° C. and stirred for 2 h. The layers were separated, and the aqueous layer extracted with CH$_2$Cl$_2$ (3×30 mL). The combined organic phases were dried over anhydrous Na$_2$SO$_4$, filtered and evaporated to give the crude product as a colourless oil. Purification by column chromatography (hexane/acetone 85:15) gave the (2R,4R)-Di-O-(3,3-pentylidene)-3-deoxy-3-hydroxymethylarabitol as a colourless oil (950 mg, 92%). R$_f$ 0.28 (hexane/acetone 80:20). [α]$_D$ −9.7 (c 1.06, CHCl3, 23° C.). 1H NMR (300 MHz, CDCl$_3$) δ 4.24-4.11 (2H, m), 4.12 (1H, dd, J=8.1, 5.9 Hz), 3.96 (1H, td, J=8.8, 5.9 Hz), 3.74-3.66 (3H, m), 3.61 (1H, dd, J=8.8, 8.1 Hz), 2.63 (1H, br s), 1.84 (1H, m), 1.67-1.54 (8H, m), 0.897 (3H, t, J=7.35 Hz), 0.890 (3H, t, J=7.35 Hz), 0.87 (3H, t, J=7.35 Hz), and 0.86 (3H, t, J=7.35 Hz).

Step 5: Synthesis of (2R,4R)-Di-O-(3,3-pentylidene)-3-deoxy-3-formylarabitol

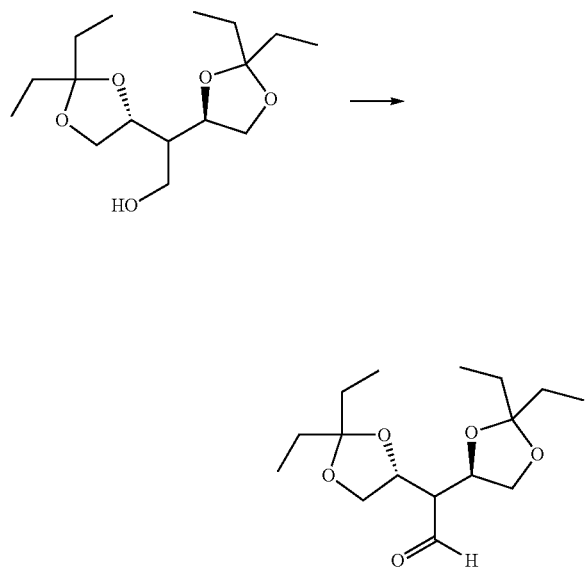

In a 250 mL 2 neck round-bottomed flask (A), was stirred a solution of the "pseudo"-C2-symmetric primary alcohol of step 4 (1.90 g, 6.28 mmol) in CH$_2$Cl$_2$ (30 mL) and DMSO (15 mL) at 0° C. In a 100 mL 2 neck roundbottomed flask (B) was stirred a solution of SO$_3$.pyridine complex (3.00 g, 18.9 mmol), and triethylamine (3.2 mL, 23.2 mmol) in CH$_2$Cl$_2$ (30 mL) and DMSO (15 mL) at 0° C. for 10 min. The contents of flask (B) were then transferred via cannula to flask (A) over a period of 10 min. The reaction mixture was then stirred at 0° C. for 1.5 h. The reaction mixture was poured into a mixture of saturated aqueous NH$_4$Cl:water:diethylether:pentane (1:1:1:1, 100 mL). The layers were separated, and the aqueous layer extracted with a diethylether:pentane mixture (1:1, 2×100 mL). The combined organic phases were dried over anhydrous Na$_2$SO$_4$, filtered and evaporated to give the crude product as a colourless oil. Purification by column chromatography (hexane/acetone 95:5) gave (2R,4R)-Di-O-(3,3-pentylidene)-3-deoxy-3-formylarabitol as a colourless oil (1.806 g, 96%). R$_f$ 0.52 (hexane/acetone 80:20). [α]$_D$ +39.5 (c 0.40, CHCl$_3$, 23° C.). 1H NMR (300 MHz, CDCl3) δ 9.83 (1H, d, J=1.5 Hz), 4.37 (1H, td, J=7.7, 5.9 Hz), 4.28-4.18 (3H, m), 3.82 (1H, m), 3.54 (1H, m), 2.60 (1H, m), 1.69-1.50 (8H, m), 0.90-0.82 (12H, m).

Step 6: Synthesis of cis-(4R,6R)-2,8-dioxa-4,6-dihydroxy bicyclo[3.3.0]octane

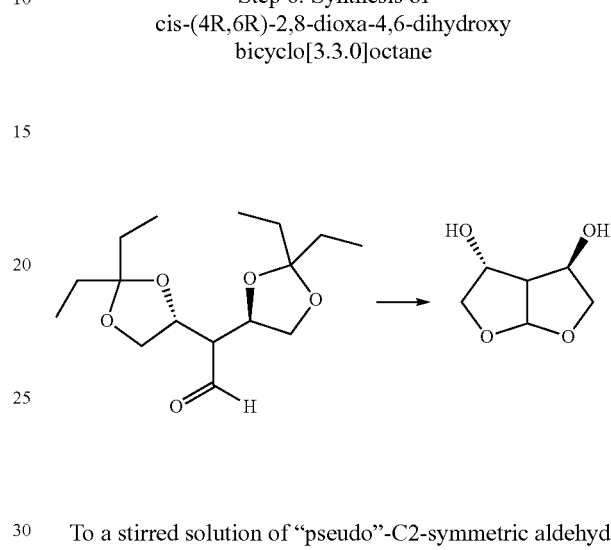

To a stirred solution of "pseudo"-C2-symmetric aldehyde (6.9 g, 22.97 mmol) in 70 mL of dichloromethane at room temperature was added 7.7 mL of a mixture of trifluoro-acetic acid and water (9:1; v/v). After 15 min the solvent was removed in vacuo and the crude was coevaporated with toluene. The purification by column chromatography (dichloromethane/methanol 9:1) gave (cis-(4R,6R)-2,8-dioxa-4,6-dihydroxy bicyclo[3.3.0]octane as a white solid (2.844 g, 85%). R$_f$ 0.24 (CH$_2$Cl$_2$/MeOH 90:10). [α]$_D$ +45.8 (c 0.61, MeOH, 24° C.). 1H NMR (400 MHz, DMSO-d6) δ 5.62 (1H, d, J=5.5 Hz), 5.22 (1H, d, J=4.5 Hz), 4.85 (1H, d, J=4.5 Hz), 4.43 (1H, t, J=4.0 Hz), 4.29 (1H, m), 3.79 (1H, d, J=9.5 Hz), 3.78 (1H, dd, J=9.0, 2.5 Hz), 3.68 (1H, d, J=9.5 Hz), 3.28 (1H, m), and 2.57 (1H, dd, J=9.0, 5.0 Hz).

The following steps 7-10 (depicted in scheme 1 as steps g-j) describes the synthesis of cis-(4R,6R)-4-benzyloxy-2,8-dioxa-6-hydroxy-bicyclo[3.3.0]octane (10) starting from cis-(4R,6R)-2,8-dioxa-4,6-dihydroxy bicyclo[3.3.0]octane (6).

Scheme 1: Synthesis of the (3R,3aR,4R,6aS)-3-Benzyl-hexahydrofuro[2,3-b]furan-4-ol (10)

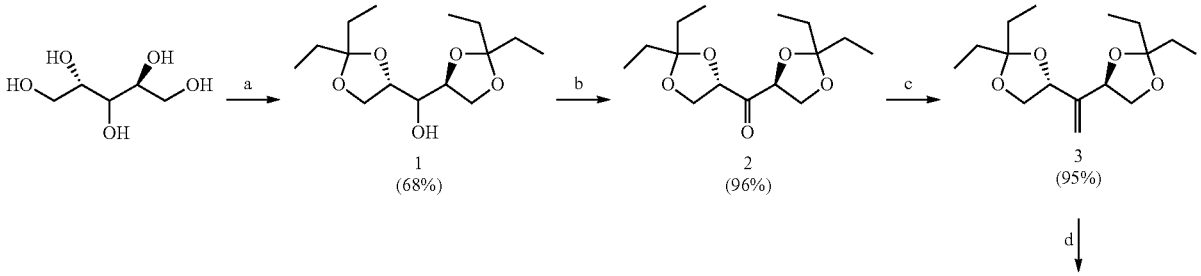

-continued

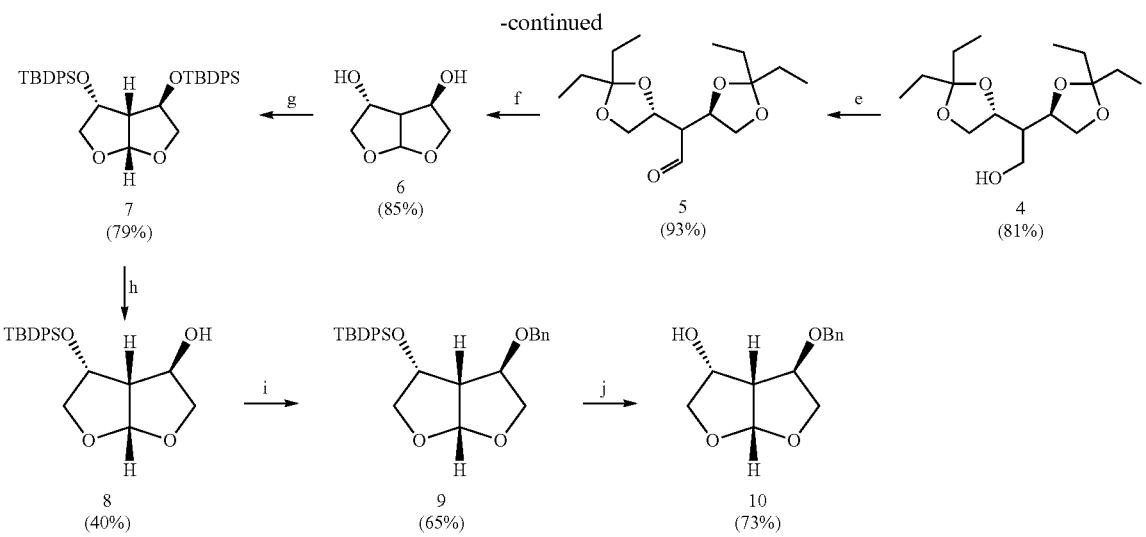

a. i. CSA (30% mol.), DMP (4.4 eq.), THF, reflux, 5 min.; ii. succinic anhydride, CH₂Cl₂, Et₃N, reflux, 1.5 h, 68%;
b. SO₃·py (3 eq.), DMSO, Et₃N, CH₂Cl₂, 0° C., 5 h, 96%;
c. Ph₃PCH₃Br (2 eq.), NaHMDS (1.9 eq.), THF, 0° C., 4 h, 95%;
d. Et₃B (3 eq.), BH₃ (0.5 eq.), THF, r.t., 2 d, 81%;
e. SO₃·py (3 eq.), DMSO, Et₃N, CH₂Cl₂, 0° C., 1.5 h, 93%;
f. TFA, CH₂Cl₂, H₂O, 85%;
g. TBDPSCl (4 eq.), DMAP (0.8 eq.), imidazole (8 eq.), DMF, r.t., 79%;
h. NH₄Cl (4 eq.), CH₃OH, r.t., 40%;
i. BnBr (3 eq.), NaH (3 eq.), TBAI (0.2 eq.), THF, 0° C., 65%;
j. TBAF (1.5 eq), THF, r.t. 73%.

| Abbreviations | |
|---|---|
| BnBr | benzyl bromide |
| CSA | camphorsulfonic acid |
| d | doublet |
| dd | doublet of doublet |
| dt | doublet of triplet |
| DMAP | 4-dimethylaminopyridine |
| DMF | dimethylformamide |
| DMP | dimethoxypentane |
| DMSO | dimethylsulfoxide |
| EtOAC | ethyl acetate |
| m | multiplet |
| NaHMDS | sodium hexamethyldisilazane |
| r.t. | room temperature |
| s | singulet |
| t | triplet |
| TBAF | tetrabutylammonium fluoride |
| TBAI | tetrabutylammonium iodide |
| TBDPSCl | tert-butyldiphenylsilyl chloride |
| TFA | trifluoroacetic acid |
| THF | tetrahydrofuran |

Step 7: Synthesis of Cis-(4R,6R)-2,8-dioxa-4,6-Bis(tert-butyldiphenylsilanoxy)-bicyclo[3.3.0]octane

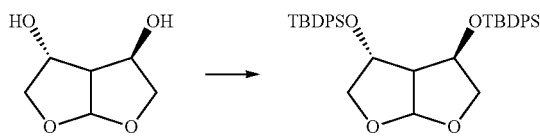

To a solution of the diol 6 (100 mg, 0.68 mmol), imidazole (372 mg, 5.48 mmol), and DMAP (66 mg, 0.54 mmol) in DMF (10 mL) was added tert-butyldiphenylsilylchloride (0.72 mL, 2.74 mmol) and was stirred at room temperature for one day. The solvent was removed on a high vacuum rotary evaporator at 40° C. and the residue was purified by column chromatography (hexane/acetone 95/5). Further purification by preparative HPLC (hexane/acetone 95:5) gave cis-(4R,6R)-2,8-dioxa-4,6-Bis(tert-butyldiphenyl silanoxy)-bicyclo[3.3.0]octane as a colourless oil (337 mg, 79%). $R_f$ 0.24 (hexane/acetone 95:5). $[\alpha]_D$ −10.5 (c 4.24, CHCl₃, 24° C.).
¹H NMR (400 MHz, CDCl₃) δ 7.73-7.70 (4H, m), 7.57-7.52 (4H, m), 7.49-7.33 (12H, m), 5.89 (1H, d, J=5.0 Hz), 4.96 (1H, d, J=2.5 Hz), 4.36 (1H, dt, J=9.5, 6.8 Hz), 4.01 (1H, dd, J=9.5, 1.0 Hz), 3.93 (1H, dd, J=9.5, 3.0 Hz), 3.40 (1H, dd, J=9.5, 6.5 Hz), 3.34 (1H, dd, J=9.5, 7.0 Hz), 2.94 (1H, dd, J=9.0, 5.0 Hz), 1.12 (9H, s), 0.91 (9H, s) ppm.

Step 8: Synthesis of Cis-(4R,6R)-2,8-dioxa-4-hydroxy-6-(tert-butyldiphenylsilanoxy)-bicyclo[3.3.0]octane Method A:

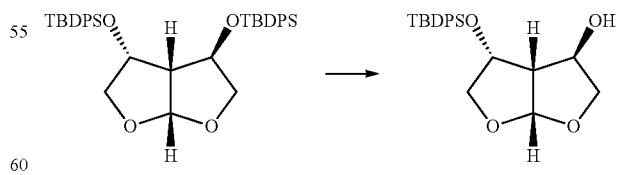

To a stirred solution of compound 7 (47 mg, 0.075 mmol) in methanol (1.5 mL) at room temperature was added NH₄F (22 mg, 0.6 mmol). After 4 days the solvent was removed in vacuo and purification by column chromatography (hexane/EtOAc 85:15) gave cis-(4R,6R)-2,8-dioxa-4-hydroxy-6-(tert-butyldiphenylsilanoxy)-bicyclo[3.3.0]-octane (8) as a colourless oil (13 mg, 45%). R$_f$ 0.76 (hexane/acetone 5:5). [α]$_D$ +18 (c 0.25, CHCl$_3$, 27° C.). $^1$H NMR (400 MHz, CDCl$_3$) δ 7.71-7.62 (4H, m), 7.49-7.39 (6 H, m), 5.71 (1H, d, J=5.0 Hz), 4.83 (1H, d, J=3.5 Hz), 4.48 (1H, dt, J=7.0, 9.0 Hz), 4.12 (1H, dd, J=4.0, 10.0 Hz), 3.97 (1H, d, J=10.0 Hz), 3.69 (1H, dd, J=7.0, 9.0 Hz), 3.48 (1H, t, J=8.5 Hz), 2.61 (1H, dd, J=5.0, 9.0 Hz), 1.92 (1H, s), 1.11 (9H, s) ppm.

Method B:

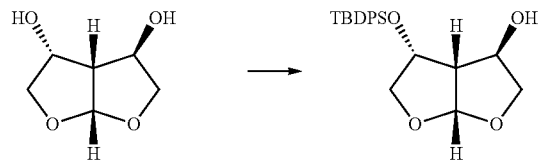

To a solution of the diol 6 (8.633 g, 0.059 mol), imidazole (32.174 g, 0.472 mol), DMAP (5.773 g, 0.047 mol) in DMF (200 mL) was added tert-butyldiphenylsilylchloride (66.18 mL, 0.236 mol) and was stirred at room temperature for one day. Once the reaction completed, 200 mL of Et$_2$O and 500 mL of water was added. The layers were separated and the organic layer washed with 300 mL of water and 300 mL of brine, then dried over anhydrous Na$_2$SO$_4$, filtered and the solvent removed in vacuo to give the crude product as colourless oil. The crude was dissolved in 400 mL of methanol and NH$_4$F (8.752 g, 0.236 mol) was added. The reaction was stirred at refluxing temperature 2.5 h, then the solvent was removed in vacuo. Purification of the crude product by column chromatography (hexane/acetone 90:10, 85:15 then 100% acetone) gave successively the protected compound 7 (not isolated pure), cis-(4R,6R)-2,8-dioxa-4-hydroxy-6-(tert-butyldiphenyl silanoxy)-bicyclo[3.3.0]octane (8) as a colourless oil (10.03 g, 44%), and the deprotected compound 6 (1.59 g, 18%).

Step 9: Synthesis of Cis-(4R,6R)-4-benzyloxy-2,8-dioxa-6-(tert-butyldiphenylsilanoxy)-bicyclo[3.3.0]octane

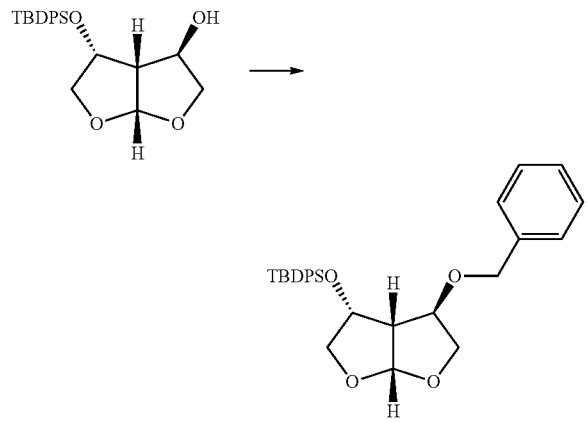

To a stirred suspension of NaH (268 mg, 7 mmol, 60% in oil) in 3 mL of THF at 0° C. was added a solution of alcohol 8 (900 mg, 2.34 mmol) in 9 mL of THF. After 10 min benzyl bromide (0.84 mL, 7 mmol) and TBAI (177 mg, 0.47 mmol) were added and the reaction was stirred at 0° C. Once completed after 4 h, 2 ml of water were added dropwise to quench the excess of NaH and the solvent was removed in vacuo. Purification of the crude product by column chromatography (hexane/AcOEt 95:5) gave cis-(4R,6R)-4-benzyloxy-2,8-dioxa-6-(tert-butyldiphenylsilanoxy)-bicyclo-[3.3.0]octane (9) as a colourless oil (725 mg, 65%). R$_f$ 0.62 (hexane/AcOEt 7:3). [α]$_D$ –10.6 (c 0.7, CHCl$_3$, 25° C.).

$^1$H NMR (400 MHz, CDCl$_3$) δ 7.58-7.50 (4H, m), 7.39-7.18 (11H, m), 5.64 (1H, d, J=5.3 Hz), 4.56 (1H, d, J=3.4 Hz), 4.40 (1H, d, J=12.0 Hz), 4.37 (1H, m), 4.32 (1 H, d, J=11.7 Hz), 4.11 (1H, J=10.0 Hz), 3.98 (1H, dd, J=9.8, 10.2 Hz), 3.55 (1H, dd, J=8.7, 6.8 Hz), 3.36 (1H, t, J=8.7 Hz), 2.76 (1H, dd, J=5.3, 9.0 Hz), 0.98 (9H, s) ppm.

Step 10: Synthesis of Cis-(4R,6R)-4-benzyloxy-2,8-dioxa-6-hydroxy-bicyclo[3.3.0]-octane

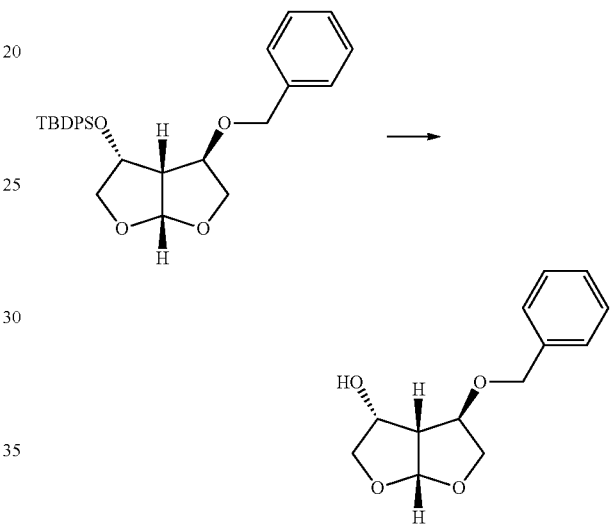

To a stirred solution of compound 9 (532 mg, 1.12 mmol) in 20 mL of THF at room temperature was added TBAF (1.68 mL, 1.68 mmol, 1M in THF). After 10 min the solvent was removed in vacuo and the purification of the crude product by column chromatography (hexane/AcOEt 80:20) gave cis-(4R,6R)-4-benzyloxy-2,8-dioxa-6-hydroxy-bicyclo[3.3.0]octane (10) as a white solid (194 mg, 73%). R$_f$ 0.58 (hexane/acetone 5:5). [α]$_D$ +74 (c 0.15, CHCl$_3$, 27° C.). $^1$H NMR (400 MHz, CDCl$_3$) δ 7.34-7.28 (5H, m), 5.83 (1H, d, J=5.0 Hz), 4.55 (3H, m), 4.48 (1H, d, J=3.8 Hz), 4.13 (1H, d, J=10.0 Hz), 4.00 (2H, m), 3.62 (1H, dd, J=7.0, 9.0 Hz), 2.93 (1H, dd, J=5.0, 8.0 Hz), 1.79 (1H, bs) ppm.

Further to the preparation of compound (10) as above described, additional compounds were prepared having the general formula:

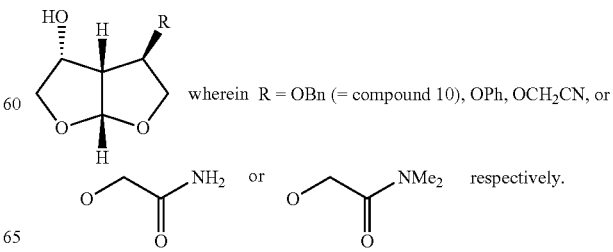

wherein R = OBn (= compound 10), OPh, OCH$_2$CN, or

NH$_2$ or NMe$_2$ respectively.

Step 11: Synthesis of {3-[(4-amino-benzenesulfo-nyl)-isobutyl-amino]-1-benzyl-2-hydroxy-propyl}-carbamic acid 4-benzyloxy-hexahydro-furo[2,3-b]furan-3-yl ester (13)

LC-MS (M+H)$^+$: 654 $^1$H NMR (400 MHz, CDCl$_3$) δ 7.54 (2H, d, J=8.68 Hz), 7.39-7.14 (10H, m), 6.67 (2H, d, J=8.61 Hz), 5.8 (1H, d, J=5.18 Hz), 5.12 (1H, ddd, J=11.87 Hz, J=6.06 Hz, J=5.81 Hz), 4.95 (1H, d, J=8.54 Hz), 4.37 (1H, d, J=11.8 Hz), 4.26 (1H, d, J=11.8 Hz), 4.15 (2H, br s), 4.08 (1H,

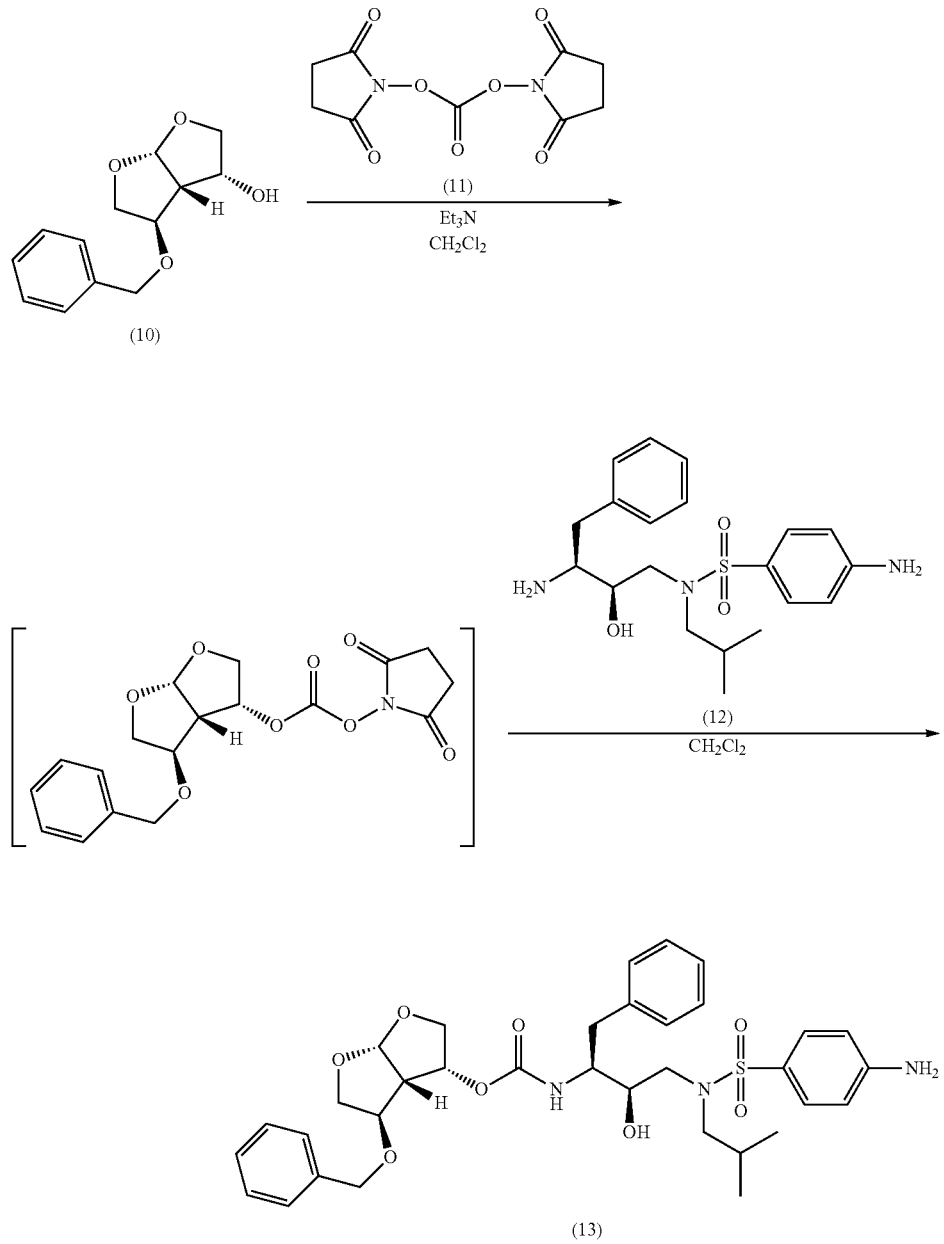

To a stirring solution of triethylamine (43 mg, 423 µmol) and carbonic acid bis-(2,5-dioxo-pyrrolidin-1-yl) ester (11) (58 mg, 226 µmol) in CH2Cl2 (5 mL) was added (10) (50 mg, 212 µmol). The mixture was stirred at RT for 4 hours. Then 4-amino-N-(3-amino-2-hydroxy-4-phenyl-butyl)-N-isobutyl-benzenesulfonamide (12) (83 mg, 212 µmol) was added at once. The mixture was stirred overnight at RT. The mixture was then separated by column chromatography using CH2Cl2→CH2Cl2/MeOH(NH$_3$) 97-3 as the eluent. After evaporation, (13) (53 mg, 81 µmol, 38%) was obtained as a white solid.

d, J=10.1 Hz) 3.98 (1H, dd, J=10.0, J=6.1 Hz), 3.91-3.80 (3H, m), 3.75-3.50 (3H, m), 3.12 (1H, dd, J=15.07, J=8.43), 3.05-2.9 (4H, m), 2.84-2.74 (2H, m), 1.81 (1H, septaplet, J=6.62), 0.87 (3H, d, J=6.58), 0.45 (3H, d, J=6.58 Hz).

The thus obtained compounds were tested in a biological assay for antiviral activity.

As an example is hereafter provided the test result for compound (13): {3-[(4-amino-benzenesulfonyl)-isobutyl-amino]-1-benzyl-2-hydroxy-propyl}-carbamic acid 4-benzyloxy-hexahydro-furo[2,3-b]furan-3-yl ester, while as reference compound has been used the compound, so-called TMC 114 or darunavir, with the following chemical structure, a new protease inhibitor under clinical investigation for the treatment of HIV-infections.

Darunavir has the following chemical name: (3R,3aS,6aR)-hexahydrofuro[2,3-b]furan-3-yl N-[(1S,2R)-1-benzyl-2-hydroxy-3-(N1-isobutylsulfanilamido)propyl]carbamate

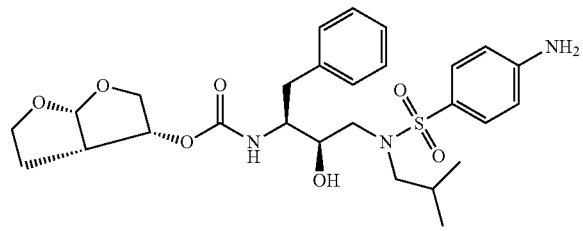

The compounds were tested in a cellular assay using the MT4-LTR-EGFP cells for anti-viral activity. The assay demonstrated that the compounds exhibit potent anti-HIV activity against a wild type laboratory HIV strain (WT IIIB-2-001) and several HIV mutant strains, indicated as mutant 1, 2, 3 and 4 in Tables 1 and 2 respectively.

The cellular assay was performed according to the following procedure. HIV- or mock-infected MT4-LTR-EGFP cells were incubated for three days in the presence of various concentrations of the compounds mentioned above. Upon infection, the viral tat protein activates the GFP reporter. At the end of the incubation period, the GFP signal was measured. In the virus control samples (in the absence of any inhibitor) the maximal fluorescent signal was obtained. The inhibitory activity of the compound was monitored on the virus-infected cells and $EC_{50}$ values were calculated. These values represent the amount of the compound required to protect 50% of the cells from virus infection. The data presented in table 1 contain the $pEC_{50}$ values, being the negative logarithm of the $EC_{50}$-values.

TABLE 1

| Compound No. | WT | Mutant 1 | Mutant 2 | Mutant 3 | Mutant 4 |
|---|---|---|---|---|---|
| TMC 114 | 8.17 | 8.09 | 6.10 | 7.05 | 5.43 |
| 13 | 8.8 | 8.0 | 6.5 | 6.9 | 5.7 |

The viral mutant strains 1-4 on which the compounds were tested contain mutations as indicated in table 2.

TABLE 2

| | |
|---|---|
| Mutant 1 | V003I, L010I, V032T, L033M, E035D, S037Y, M046I, R057R/K, Q058E, L063P, K070T, A071V, I072V, I084V, L089V |
| Mutant 2 | V003I, V032I, L035D, M036I, S037N, K043T, M046I, I047V, I050V, K055R, I057K, I062V, L063P, A071L, V082I, I085V, L090M, I093L |
| Mutant 3 | V003I L010I I013V G016A/G L019I L033F S037N M046I I050V F053L I054V K055R L063P A071V G073C V077I/V V082A L090M |
| Mutant 4 | V003I L010F I013V V032T S037N M046I I047V I050V L063P A071V I084V L089V T091A Q092R |

The invention claimed is:

1. A compound having the formula (II) or a stereoisomer thereof,

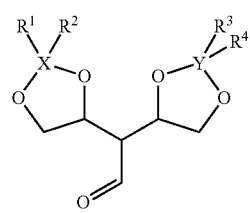

wherein
X and Y are independently selected from Si and C; and,
$R^1$, $R^2$, $R^3$ and $R^4$ are independently selected from the group consisting of —H and monovalent hydrocarbon radicals;
$R^1$ and $R^2$ can be taken together to form a bivalent hydrocarbon radical represented by —$R^1$-$R^2$—;
$R^3$ and $R^4$ can be taken together to form a bivalent hydrocarbon radical represented by —$R^3$-$R^4$—;
or a salt form thereof.

2. A compound according to claim 1 wherein the compound is one of the following stereoisomers

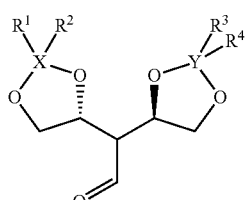

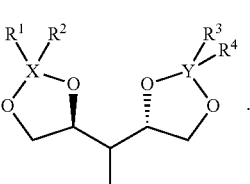

3. A process for the production of a compound as described in claim 1 comprising oxidizing a compound having the formula (III)

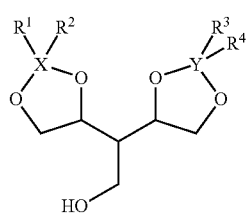

wherein
X and Y are independently selected from Si and C; and,
$R^1$, $R^2$, $R^3$ and $R^4$ are independently selected from the group consisting of —H and monovalent hydrocarbon radicals;

R¹ and R² can be taken together to form a bivalent hydrocarbon radical represented by —R¹-R²—;

R³ and R⁴ can be taken together to form a bivalent hydrocarbon radical represented by —R³-R⁴—;

to obtain a compound of formula (II).

4. A compound according to claim 1, wherein X and Y are the same and are C.

5. A compound according to claim 1, wherein R¹, R², R³ and R⁴ are independently selected from the group consisting of —H, $C_{1-20}$alkyl, $C_{2-20}$alkenyl, $C_{2-20}$alkoxyalkyl, $C_{7-20}$alkoxyaryl, $C_{2-20}$alkynyl, $C_{3-30}$cycloalkyl, $C_{4-30}$(cycloalkyl)alkyl, $C_{4-30}$(cycloalkenyl)alkyl, $C_{9-30}$(cycloalkynyl)alkyl, $C_{3-30}$cycloalkenyl, $C_{4-30}$cycloalkynyl, $C_{7-30}$arylalkyl, $C_{7-30}$alkylaryl, $C_{6-30}$aryl, $C_{6-30}$heterocyclylalkyl, $C_{6-30}$alkylheterocyclyl and $C_{5-3}$heterocyclyl.

6. A compound according to claim 1, wherein R¹, R², R³ and R⁴ are independently selected from the group consisting of —H, primary or secondary $C_{1-6}$alkyl, $C_{2-6}$alkenyl, $C_{1-6}$alkoxy$C_{1-6}$alkyl, $C_{1-6}$alkoxy$C_{5-10}$aryl, $C_{5-7}$cycloalkyl, $C_{5-11}$cycloalkyl$C_{1-6}$alkyl, $C_{4-11}$cycloalkenyl$C_{1-6}$alkyl, $C_{8-12}$cycloalkynyl$C_{1-6}$alkyl, $C_{5-7}$cycloalkenyl, $C_{5-7}$cycloalkynyl, $C_{6-11}$aryl$C_{1-6}$alkyl, $C_{1-6}$alkyl$C_{6-11}$aryl, $C_{6-11}$aryl, $C_{5-12}$heterocyclyl$C_{1-6}$alkyl, $C_{1-6}$alkyl$C_{5-12}$heterocyclyl and $C_{5-12}$heterocyclyl.

7. A compound according to claim 1, wherein R¹, R², R³ and R⁴ are the same.

8. A compound according to claim 1, wherein X and Y are C and R¹, R², R³ and R⁴ are the same and are selected from the group consisting of methyl, ethyl, n-propyl, s-propyl, n-butyl, s-butyl, t-butyl, benzyl, phenyl and methoxyphenyl.

9. A process for the production of a compound as described in claim 2 comprising oxidizing a compound having the formula (III)

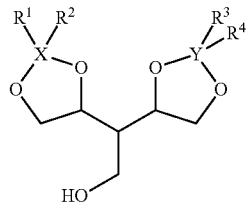

(III)

wherein

X and Y are independently selected from Si and C; and,

R¹, R², R³ and R⁴ are independently selected from the group consisting of —H and monovalent hydrocarbon radicals;

R¹ and R² can be taken together to form a bivalent hydrocarbon radical represented by —R¹-R²—;

R³ and R⁴ can be taken together to form a bivalent hydrocarbon radical represented by —R³-R⁴—;

to obtain a compound of formula (II).

10. A process according to claim 3, wherein the oxidation is carried out using Swern, Pfitzner-Moffatt or Parikh-Doering conditions.

* * * * *